US009321738B2

(12) United States Patent
Gabriel et al.

(10) Patent No.: US 9,321,738 B2
(45) Date of Patent: Apr. 26, 2016

(54) N-ALKYLTRIAZOLE COMPOUNDS AS LPAR ANTAGONISTS

(71) Applicant: Hoffmann-La Roche Inc., Nutley, NJ (US)

(72) Inventors: Stephen Deems Gabriel, Morristown, NJ (US); Matthew Michael Hamilton, Hackettstown, NJ (US); Matthew C. Lucas, Lexington, MA (US); Yimin Qian, Wayne, NJ (US); Achyutharao Sidduri, West Orange, NJ (US)

(73) Assignee: HOFFMAN-LA ROCHE INC., Nutley, NJ (US)

( * ) Notice: Subject to any disclaimer, the term of this patent is extended or adjusted under 35 U.S.C. 154(b) by 6 days.

(21) Appl. No.: 14/401,009

(22) PCT Filed: Jun. 17, 2013

(86) PCT No.: PCT/EP2013/062461
§ 371 (c)(1),
(2) Date: Nov. 13, 2014

(87) PCT Pub. No.: WO2013/189864
PCT Pub. Date: Dec. 27, 2013

(65) Prior Publication Data
US 2015/0133511 A1   May 14, 2015

Related U.S. Application Data

(60) Provisional application No. 61/661,961, filed on Jun. 20, 2012.

(51) Int. Cl.
C07D 403/00 (2006.01)
C07D 249/04 (2006.01)
C07D 249/06 (2006.01)

(52) U.S. Cl.
CPC ............ C07D 249/04 (2013.01); C07D 249/06 (2013.01)

(58) Field of Classification Search
CPC .. C07D 249/06; C07D 249/04; C07D 487/04; C08K 5/3472; A61Q 17/04
USPC .......................................... 548/255; 514/359
See application file for complete search history.

(56) References Cited

U.S. PATENT DOCUMENTS

2011/0082164 A1   4/2011   Clark et al.

FOREIGN PATENT DOCUMENTS

| WO | 2011029803 | 3/2011 | |
| WO | 2011159550 | 12/2011 | |
| WO | 2011159633 | 12/2011 | |
| WO | 2012078593 | 6/2012 | |
| WO | WO 2012078593 A2 * | 6/2012 | ............ C07C 62/32 |
| WO | 2012138648 | 10/2012 | |
| WO | 2013025733 | 2/2013 | |

OTHER PUBLICATIONS

The International Search Report and Written Opinion, mailed on Sep. 2, 2013, in the corresponding PCT Appl. No. PCT/EP13/62461.
Swaney et al., "Pharmacokinetic and Pharmacodynamic Characterization of an Oral Lysophosphatidic Acid Type 1 Receptor-Selective Antagonist," JPET 336:693-700, 2011.
Swaney et al., "A novel, orally active LPA1 receptor antagonist inhibits lung fibrosis in the mouse bleomycin modelbph," British Journal of Pharmacology (2010), 160, 1699-1713.
Qian et al., "Discovery of Highly Selective and Orally Active Lysophosphatidic Acid Receptor•1 Antagonists with Potent Activity on Human Lung Fibroblasts," J. Med. Chem. 2012, 55, 7920-7939.

* cited by examiner

Primary Examiner — Nyeemah A Grazier
Assistant Examiner — Sagar Patel

(57) ABSTRACT

Provided herein are compounds of the formula (I):

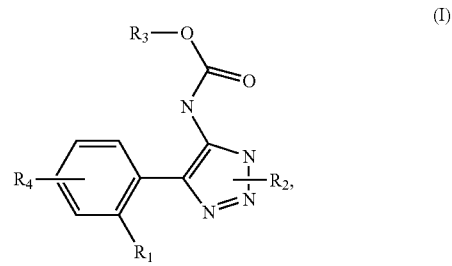

as well as pharmaceutically acceptable salts thereof, wherein the substituents are as those disclosed in the specification. These compounds, and the pharmaceutical compositions containing them, are useful for the treatment of inflammatory diseases and disorders such as, for example, pulmonary fibrosis.

13 Claims, No Drawings

N-ALKYLTRIAZOLE COMPOUNDS AS LPAR ANTAGONISTS

This application is a National Stage Application of PCT/EP2013/062461 filed Jun. 17, 2013, which claims priority from U.S. Provisional Patent Application No. 61/661,961, filed on Jun. 20, 2012. The priority of both said PCT and U.S. Provisional Patent Application are claimed. Each of prior mentioned applications is hereby incorporated by reference herein in its entirety.

The present invention relates to organic compounds useful for therapy and/or prophylaxis in a mammal of an inflammatory disease or disorder, and in particular to N-alkyltriazole compounds, their manufacture, pharmaceutical compositions containing them and their use as lysophosphatidic acid (LPA) antagonists.

LPA is a family of bioactive phosphate lipids which function like a growth factor mediator by interacting with LPA receptors, a family of G-protein-coupled receptors (GPCRs). The lipid family has long chain saturated (such as C18:0 or C16:0) or unsaturated (C18:1 or C20:4) carbon chains attached to the glycerol through an ester linkage. In biological systems, LPA is produced by multi-step enzymatic pathways through the de-esterification of membrane phospholipids. Enzymes that contribute to LPA synthesis include lysophospholipase D (lysoPLD), autotaxin (ATX), phospholipase A1 (PLA1), phospholipase A2 (PLA2) and acylglycerol kinase (AGK) (British J. of Pharmacology 2012, 165, 829-844).

There are at least six LPA receptors identified (LPAR1-6). LPA signaling exerts a broad range of biological responses on many different cell types, which can lead to cell growth, cell proliferation, cell migration and cell contraction. Up regulation of the LPA pathway has been linked to multiple diseases, including cancer, allergic airway inflammation, and fibrosis of the kidney, lung and liver. Therefore, targeting LPA receptors or LPA metabolic enzymes could provide new approaches towards the treatment of medically important diseases that include neuropsychiatric disorders, neuropathic pain, infertility, cardiovascular disease, inflammation, fibrosis, and cancer (Annu Rev. Pharmacol. Toxicol. 2010, 50, 157-186; J. Biochem. 2011, 150, 223-232).

Fibrosis is the result of an uncontrolled tissue healing process leading to excessive accumulation of extracellular matrix (ECM). Recently it was reported that the LPA1 receptor was over expressed in idiopathic pulmonary fibrosis (IPF) patients. Mice with LPA1 receptor knockout were protected from bleomycin-induced lung fibrosis (Nature Medicine 2008, 14, 45-54). Thus, antagonizing LPA1 receptor may be useful for the treatment of fibrosis, such as renal fibrosis, pulmonary fibrosis, arterial fibrosis and systemic sclerosis.

In an embodiment of the present invention, provided are compounds of general formula (I):

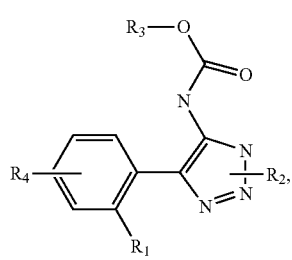

wherein:
$R_1$ is hydrogen or halogen;
$R_2$ is unsubstituted lower alkyl;
$R_3$ is unsubstituted lower alkyl, lower alkyl substituted with unsubstituted phenyl or lower alkyl substituted with phenyl substituted with trifluoromethyl; and
$R_4$ is hydrogen, halogen, cycloalkyl acetic acid, unsubstituted phenyl or phenyl substituted with a moiety selected from acetic acid, cyclopropanecarboxylic acid, cyclopropanecarboxylic acid methyl ester, methanesulfonylaminocarbonyl-cyclopropane and cyclopropyltetrazole,
or a pharmaceutically acceptable salt thereof.

In a further embodiment of the invention, provided is a pharmaceutical composition comprising a therapeutically effective amount of a compound according to formula (I) and a therapeutically inert carrier.

In a still further embodiment of the invention, provided is a method for the treatment or prophylaxis of pulmonary fibrosis, which method comprises the step of administering a therapeutically effective amount of a compound according to formula (I) to a patient in need thereof.

All documents cited to or relied upon below are expressly incorporated herein by reference.

Unless otherwise indicated, the following specific terms and phrases used in the description and claims are defined as follows:

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl and the like. In a preferred embodiment, the "cycloalkyl" moieties can optionally be substituted with one, two, three or four substituents, with the understanding that said substituents are not, in turn, substituted further. Each substituent can independently be, for example, alkyl, alkoxy, halogen, amino, hydroxyl or oxygen (O═) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. Examples of such groups include, but are not limited to, pyridine, thiazole and pyranyl.

The alkyl, lower alkyl, aryl and heteroaryl groups described above may be substituted independently with one, two, or three substituents, with the understanding that said substituents are not, in turn, substituted further. Substituents may include, for example, halogen, lower alkyl, —$CF_3$, —$SO_2CH_3$, alkoxy, —$C(O)CH_3$, —OH, —$SCH_3$ and —$CH_2CH_2OH$.

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further.

As used herein, the term "halogen" means a fluorine, chlorine, bromine or iodine radical, preferably a fluorine, chlorine or bromine radical, and more preferably a fluorine or bromine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

In one embodiment of the present invention, provided is a compound of formula (I) wherein $R_1$ is hydrogen.

In another embodiment of the present invention, provided is a compound of formula (I) wherein $R_1$ is bromine or fluorine.

In another embodiment of the present invention, provided is a compound of formula (I) wherein $R_2$ is methyl.

In another embodiment of the present invention, provided is a compound of formula (I) wherein $R_3$ is ethyl or dimethylpropyl.

In another embodiment of the present invention, provided is a compound of formula (I) wherein $R_3$ is ethyl substituted with unsubstituted phenyl.

In another embodiment of the present invention, provided is a compound of formula (I) wherein $R_3$ is ethyl substituted with phenyl substituted with trifluoromethyl.

In another embodiment of the present invention, provided is a compound of formula (I) wherein $R_4$ is hydrogen, bromine or unsubstituted phenyl.

In another embodiment of the present invention, provided is a compound of formula (I) wherein $R_4$ is phenyl substituted with a moiety selected from acetic acid, cyclopropanecarboxylic acid and cyclopropanecarboxylic acid methyl.

In another embodiment the present invention provides compounds having the general formula (I), wherein $R_1$ is halogen, in particular fluorine; $R_2$ is unsubstituted lower alkyl; $R_3$ is unsubstituted lower alkyl, lower alkyl substituted with unsubstituted phenyl or lower alkyl substituted with phenyl substituted with trifluoromethyl; and $R_4$ is hydrogen, halogen, cycloalkyl acetic acid, unsubstituted phenyl or phenyl substituted with a moiety selected from acetic acid, cyclopropanecarboxylic acid and cyclopropanecarboxylic acid methyl ester, methanesulfonylaminocarbonyl-cyclopropane and cyclopropyltetrazole, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl or lower alkyl substituted with phenyl substituted with trifluoromethyl; and $R_4$ is hydrogen, halogen, cycloalkyl acetic acid, unsubstituted phenyl or phenyl substituted with a moiety selected from acetic acid, cyclopropanecarboxylic acid and cyclopropanecarboxylic acid methyl ester, methanesulfonylaminocarbonyl-cyclopropane and cyclopropyltetrazole, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl, lower alkyl substituted with unsubstituted phenyl or lower alkyl substituted with phenyl substituted with trifluoromethyl; and $R_4$ is halogen, in particular bromine, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl, lower alkyl substituted with unsubstituted phenyl or lower alkyl substituted with phenyl substituted with trifluoromethyl; and $R_4$ is cycloalkyl acetic acid, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl, lower alkyl substituted with unsubstituted phenyl or lower alkyl substituted with phenyl substituted with trifluoromethyl; and $R_4$ is phenyl substituted with a moiety selected from acetic acid, cyclopropanecarboxylic acid and cyclopropanecarboxylic acid methyl ester, methanesulfonylaminocarbonyl-cyclopropane and cyclopropyltetrazole, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl, lower alkyl substituted with unsubstituted phenyl or lower alkyl substituted with phenyl substituted with trifluoromethyl; and $R_4$ is phenyl substituted with acetic acid, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl, lower alkyl substituted with unsubstituted phenyl or lower alkyl substituted with phenyl substituted with trifluoromethyl; and $R_4$ is phenyl substituted with cyclopropanecarboxylic acid, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl; and $R_4$ is phenyl substituted with cyclopropanecarboxylic acid, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is lower alkyl substituted with phenyl substituted with trifluoromethyl; and $R_4$ is phenyl substituted with cyclopropanecarboxylic acid methyl ester, or a pharmaceutically acceptable salt thereof.

In another embodiment the present invention provides compounds having the general formula (I) wherein $R_1$ is halogen; $R_2$ is unsubstituted lower alkyl; $R_3$ is lower alkyl substituted with unsubstituted phenyl; and $R_4$ is phenyl substituted with cyclopropanecarboxylic acid, or a pharmaceutically acceptable salt thereof.

In another embodiment the present invention provides compounds having the general formula (I) wherein $R_1$ is halogen; $R_2$ is unsubstituted lower alkyl in position 3; $R_3$ is lower alkyl substituted with unsubstituted phenyl; and $R_4$ is phenyl substituted with cyclopropanecarboxylic acid, or a pharmaceutically acceptable salt thereof.

In another embodiment the present invention provides compounds having the general formula (I) wherein $R_1$ is halogen; $R_2$ is unsubstituted lower alkyl; $R_3$ is lower alkyl substituted with unsubstituted phenyl; and $R_4$ is phenyl substituted in position 3 with cyclopropanecarboxylic acid, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is unsubstituted lower alkyl, lower alkyl substituted with unsubstituted phenyl or lower alkyl substituted with phenyl substituted with trifluoromethyl; and $R_4$ is phenyl substituted with methanesulfonylaminocarbonyl-cyclopropane, or a pharmaceutically acceptable salt thereof.

In another embodiment the present invention provides compounds having the general formula (I) wherein $R_1$ is hydrogen or halogen; $R_2$ is unsubstituted lower alkyl; $R_3$ is lower alkyl substituted with phenyl substituted with trifluoromethyl; and $R_4$ is phenyl substituted with methanesulfonylaminocarbonyl-cyclopropane, or a pharmaceutically acceptable salt thereof.

Particular compounds of formula (I) include the following:
[5-(4-Bromo-phenyl)-3-methyl-3H-[1,2,3]triazol-4-yl]-carbamic acid (R)-1-phenyl-ethyl ester;
1-{4'-[1-Methyl-5-((R)-1-phenyl-ethoxycarbonylamino)-1H-[1,2,3]triazol-4-yl]-biphenyl-4-yl}-cyclopropanecarboxylic acid;
{4'-[1-Methyl-5-((R)-1-phenyl-ethoxycarbonylamino)-1H-[1,2,3]triazol-4-yl]-biphenyl-4-yl}-acetic acid;
1-(4'-{1-Methyl-5-[1-(3-trifluoromethyl-phenyl)-ethoxycarbonylamino]-1H-[1,2,3]triazol-4-yl}-biphenyl-4-yl)-cyclopropanecarboxylic acid;

1-(4'-{1-Methyl-5-[(S)-1-(3-trifluoromethyl-phenyl)-ethoxycarbonylamino]-1H-[1,2,3]triazol-4-yl}-biphenyl-4-yl)-cyclopropanecarboxylic acid;
1-(4'-{1-Methyl-5-[(R)-1-(3-trifluoromethyl-phenyl)-ethoxycarbonylamino]-1H-[1,2,3]triazol-4-yl}-biphenyl-4-yl)-cyclopropanecarboxylic acid;
1-{4'-[5-((R)-1,2-Dimethyl-propoxycarbonylamino)-1-methyl-1H-[1,2,3]triazol-4-yl]-biphenyl-4-yl}-cyclopropanecarboxylic acid;
1-{4'-[3-Methyl-5-((R)-1-phenyl-ethoxycarbonylamino)-3H-[1,2,3]triazol-4-yl]-biphenyl-4-yl}-cyclopropanecarboxylic acid;
(R)-1-(4'-(1-Methyl-5-((1-phenylethoxy)carbonylamino)-1H-1,2,3-triazol-4-yl)biphenyl-3-yl)cyclopropanecarboxylic acid;
1-{3'-Fluoro-4'-[1-methyl-5-((R)-1-phenyl-ethoxycarbonylamino)-1H-[1,2,3]triazole-4-yl]-biphenyl-4-yl}-cyclopropanecarboxylic acid methyl ester;
1-{3'-Fluoro-4'-[1-methyl-5-((R)-1-phenyl-ethoxycarbonylamino)-1H-[1,2,3]triazole-4-yl]-biphenyl-4-yl}-cyclopropanecarboxylic acid;
{5-[4'-(1-Methanesulfonylaminocarbonyl-cyclopropyl)-biphenyl-4-yl]-3-methyl-3H-[1,2,3]triazol-4-yl}-carbamic acid (R)-1-phenyl-ethyl ester;
{5-[4'-(1-Methanesulfonylaminocarbonyl-cyclopropyl)-biphenyl-4-yl]-3-methyl-3H-[1,2,3]triazol-4-yl}-carbamic acid (R)-1-(3-trifluoromethyl-phenyl)-ethyl ester; and
(4-{4-[1-Methyl-5-((R)-1-phenyl-ethoxycarbonylamino)-1H-[1,2,3]triazol-4-yl]-phenyl}-cyclohexyl)-acetic acid.

In another embodiment of the invention, provided is a compound of formula (I) for use as a therapeutically active substance.

In another embodiment of the invention, provided is pharmaceutical composition comprising a therapeutically effective amount of a compound of formula (I) and a therapeutically inert carrier.

In another embodiment of the invention, provided is a use of a compound according to formula (I) for the treatment or prophylaxis of pulmonary fibrosis.

In another embodiment of the invention, provided is a use of a compound according to formula (I) for the preparation of a medicament for the treatment or prophylaxis of pulmonary fibrosis.

In another embodiment of the invention, provided is a compound according to formula (I) for the treatment or prophylaxis of pulmonary fibrosis.

In another embodiment of the invention, provided is compound according formula (I), when manufactured according to a process below.

In another embodiment of the invention, provided is a method for the treatment or prophylaxis of pulmonary fibrosis, which method comprises the step of administering a therapeutically effective amount of a compound of formula (I) to a patient in need thereof.

In another embodiment of the invention, provided is an invention as hereinbefore described.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials, or utilizing general synthetic techniques and procedures known to those skilled in the art. Chemicals may be purchased from companies such as for example Aldrich, Argonaut Technologies, VWR, Lancaster, Princeton, Alfa, Oakwood, TCI, Fluorochem, Apollo, Matrix, Maybridge or Meinoah. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography. Final compounds and intermediates were named using the AutoNom2000 feature in the MDL ISIS Draw application.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phosphodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

The compounds of the present invention can be prepared by any conventional means. Suitable processes for synthesizing these compounds are provided in the examples. Generally, compounds of formula I can be prepared according to the schemes illustrated below. For example, certain compounds of the invention may be made using the approaches outlined in Schemes 1 to 7.

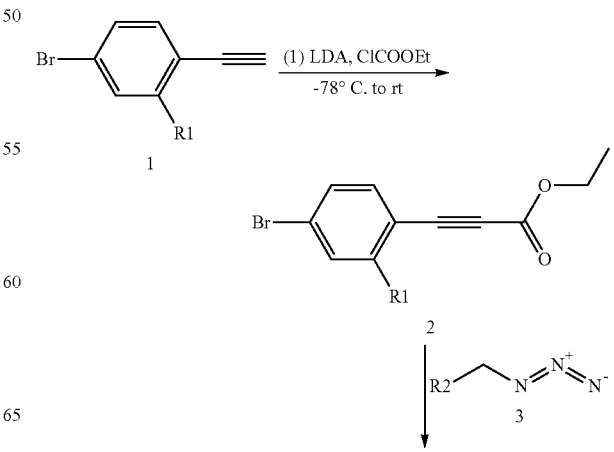

Scheme 1

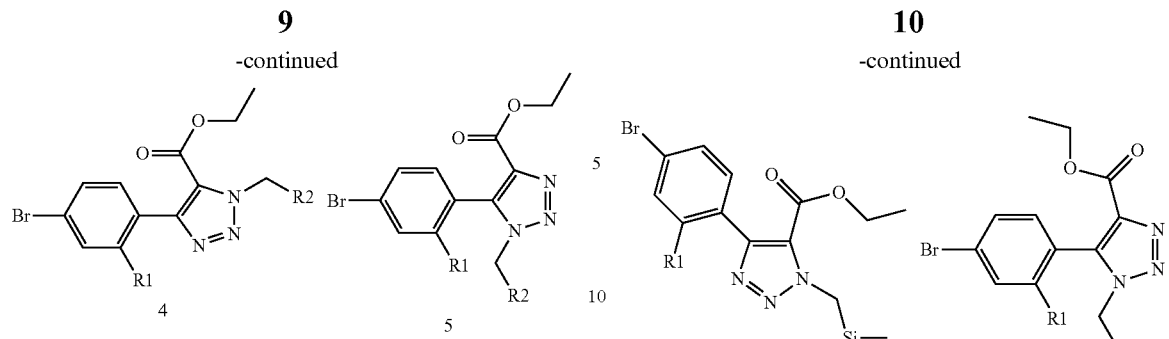

The construction of aryl-substituted N-alkyltriazole core is described in Scheme 1. Under strong basic condition, such as LDA, deprotonation of arylacetylene 1 followed by reaction with chloroformate, such as ethyl chloroformate, can provide aryl acetylene carboxylic acid ethyl ester 2, where R1 can be hydrogen, halogen or lower alkoxy groups. The reaction of compound 2 with alkylazide 3 can provide two triazole isomers 4 and 5, where R2 can be lower alkyl groups, such as methyl group. Compound 3 and 4 can be separated from the reaction mixture, and their structure assignment can be confirmed from proton NOE experiment.

Scheme 2

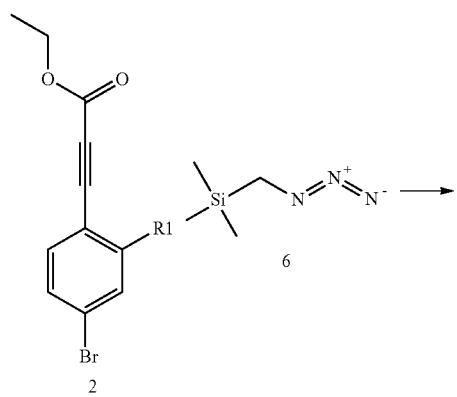

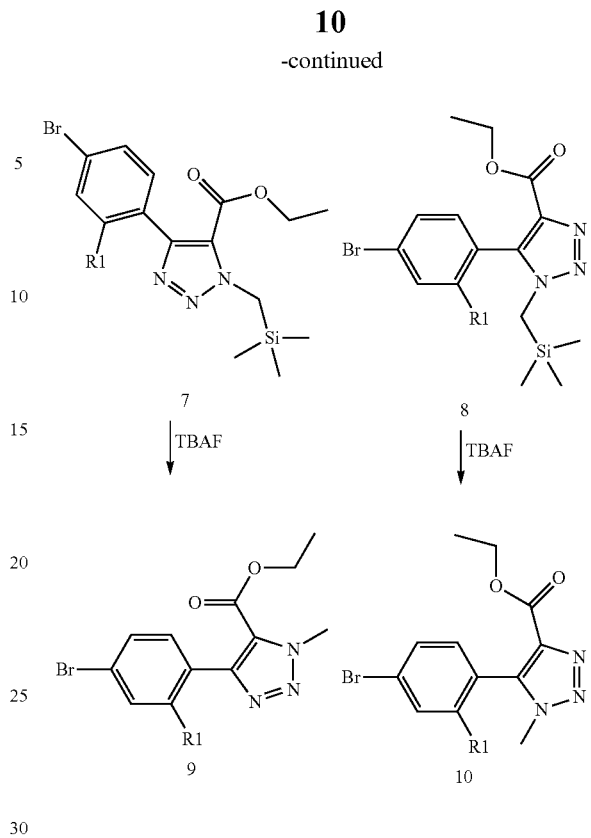

Alternatively, when R2 is hydrogen in compound 4 and 5, the synthesis of the triazole core is described in Scheme 2. Arylacetylene carboxylic acid ester 2 can react with trimethylsilymethylazide 6 to form triazole isomers 7 and 8. Compound 7 and 8 can be separated, and their chemical structures can be confirmed from proton NOE experiments. Treatment of compound 7 or 8 with tetrabutylammonium fluoride (TBAF) can deprotect the sily group to provide compound 9 or 10.

Scheme 3

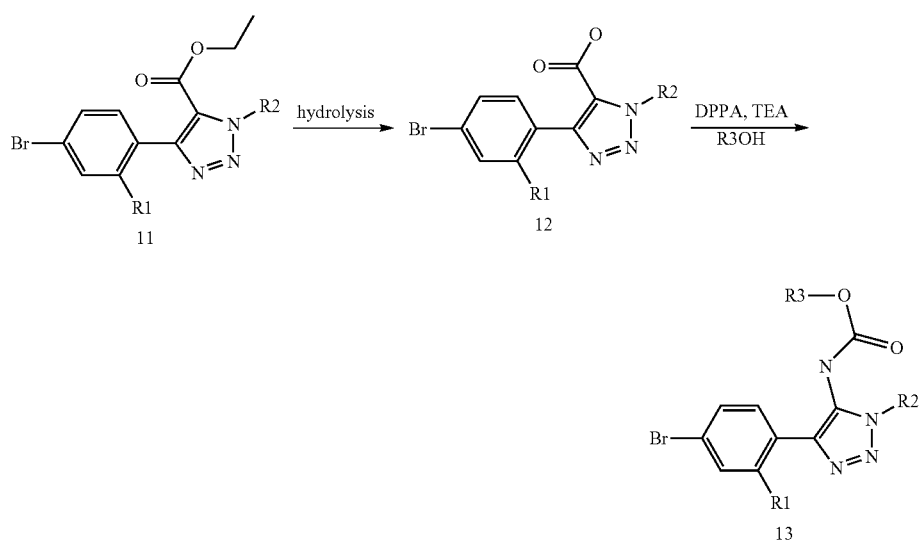

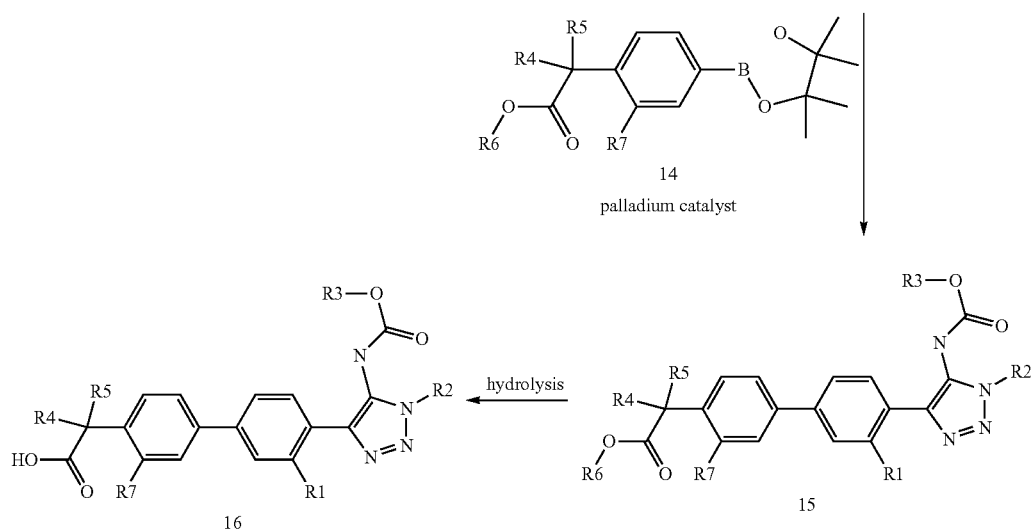

As described in Scheme 3, the aryl-substituted triazole carboxylic acid ester 11 can be hydrolyzed under basic condition to give the corresponding carboxylic acid 12, where R1 can be H, halogen and lower alkoxy groups, and R2 can be lower alkyl groups, such as methyl or ethyl groups. Compound 12 can be converted to the corresponding carbamate 13 through Curtis reaction in the presence of diphenylphosporylazide (DPPA), substituted alcohol, and base, such as triethylamine (TEA), where R3 can be alkyl group or aryl-substituted alkyl groups. Coupling of compound 13 with aryl-substituted boronic acid pinacol ester 14 under Suzuki aryl-aryl coupling conditions catalyzed by palladium catalyst can provide the biaryl intermediate 15, where R4 and R5 can be hydrogen, lower alkyl groups, such as methyl group. R4 and R5 in boronate 14 can also be connected to form a ring, such as 3-membered, 4-membered or 5-membered carbocyclic ring, R7 can be hydrogen or halogen, such as fluorine. Hydrolysis of compound 15 under basic conditions can provide the desired carboxylic acid 16.

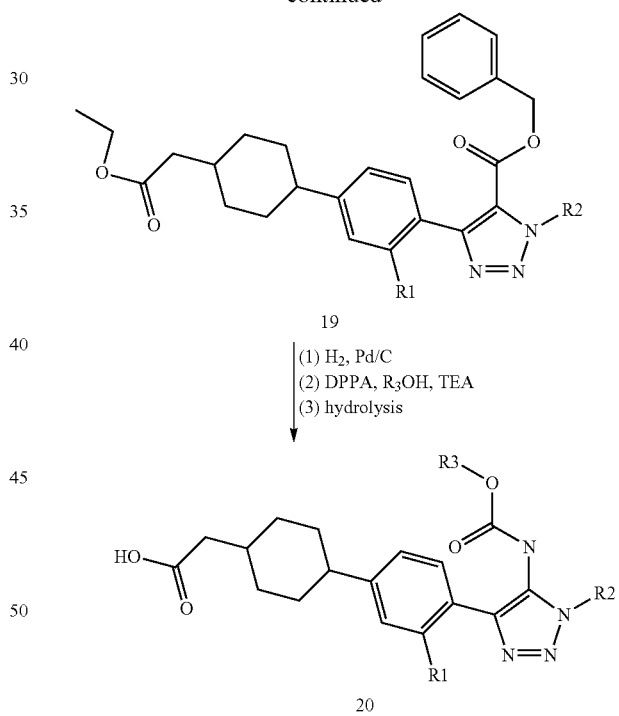

To prepare the cycloalkyl acetic acid, such as compound 20 in Scheme 4, the cycloalkylalcohol, such as 4-hydroxycyclohexylacetic acid ethyl ester 17, can be converted to the corresponding iodide 18 by using iodine and triphenylphosphine. The cycloalkyliodide 18 can be converted to the corresponding cycloalkylzinc halide, which can be coupled to aryl halide 21 under Neigishi coupling conditions to provide compound 19, where R1 and R2 are defined in Scheme 3. Hydrogenation of 19 followed by Curtis rearrangement and hydrolysis can provide the desired cycloalkylcarboxylic acid 20.

Scheme 4

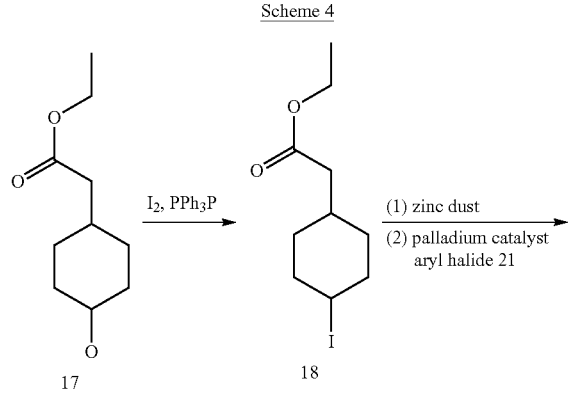

Scheme 5

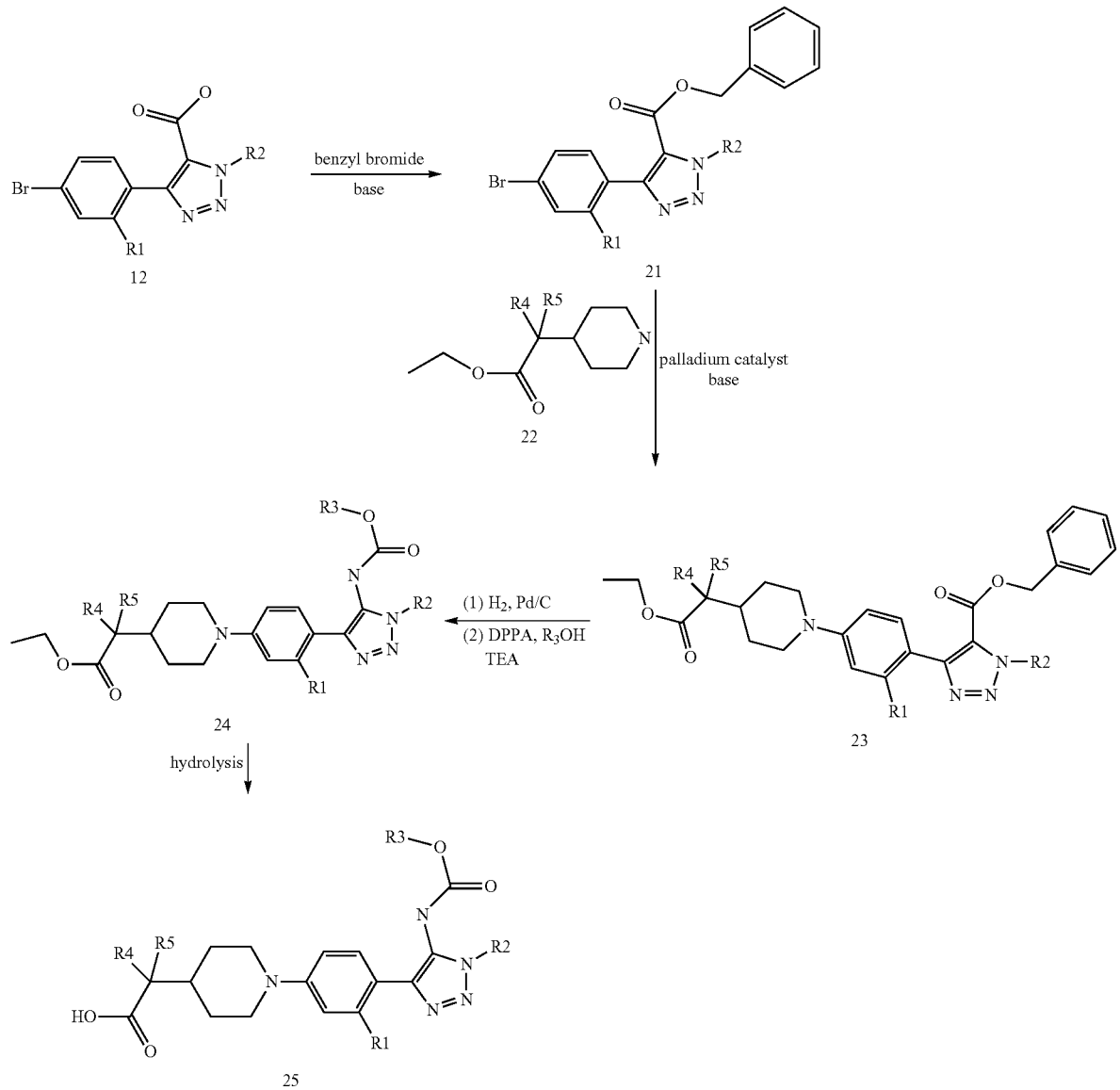

To prepare the heterocycle substituted carboxylic acid 25 in Scheme 5, carboxylic acid 12 can be converted to the corresponding benzyl ester 21 in the presence of benzyl bromide and base. Under Buchwald amination conditions, compound 21 can be coupled with cyclic amine 22 in the presence of palladium catalyst to give the desired coupling product 23. R4 and R5 in compound 22 can be hydrogen, and R4 and R5 can be connected to form a ring such as a 3-membered ring. When R4 and R5 are connected to form a cyclopropane ring, the cyclic amine 22 can be prepared according to the literature procedure (WO2008/053194). Hydrogenation of 23 followed by Curtis rearrangement reaction can lead to the desired carbamate 24, which can be further hydrolyzed to form the desired carboxylic acid 25.

Scheme 6

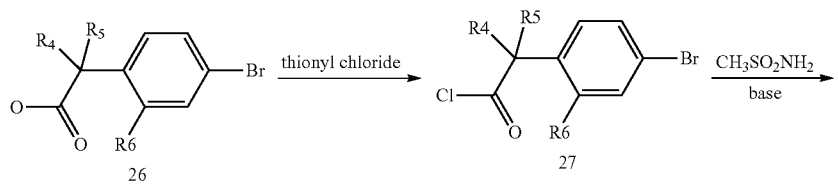

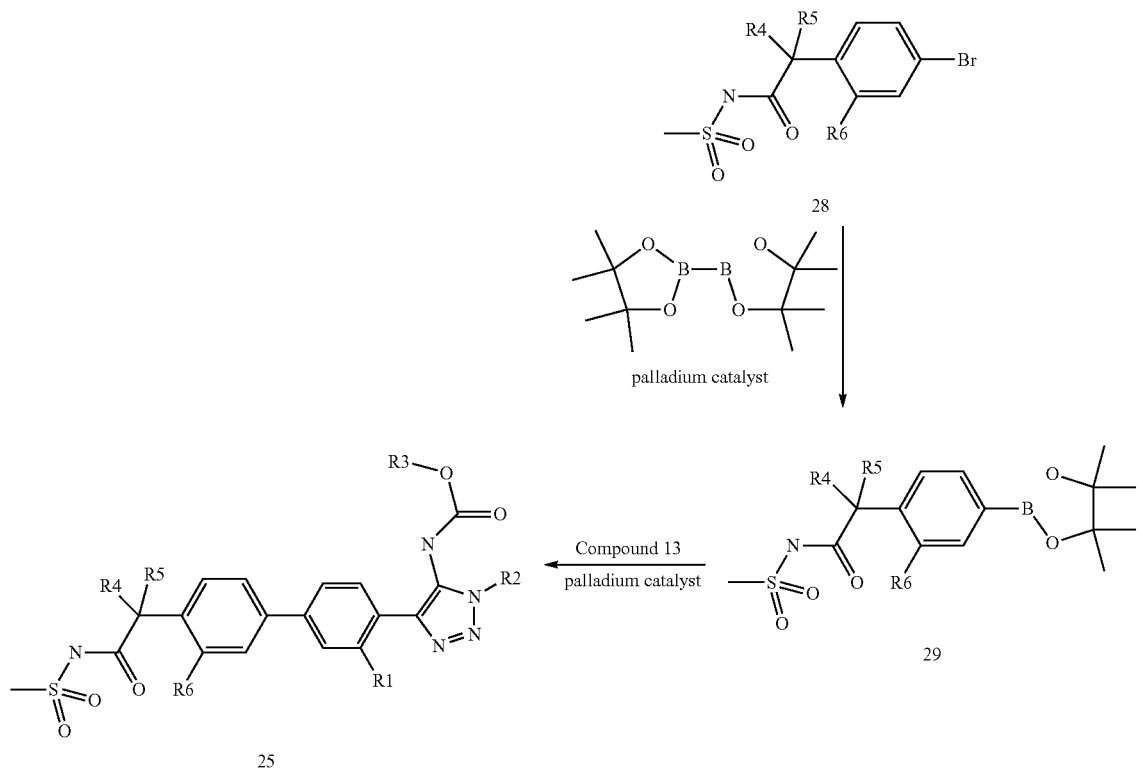

To prepare compound 30 in Scheme 6, phenylacetic acid derivative 26 can be converted to its acyl chloride 27 by reacting with thionyl chloride, which can be further converted to its corresponding acylsulfonamide 28 in the presence of methanesulfonamide and base. The arylbromide 28 can be converted to the corresponding pinacol boronate 29, which can be coupled with compound 13 to provide the desired N-acylsulfonamide 30.

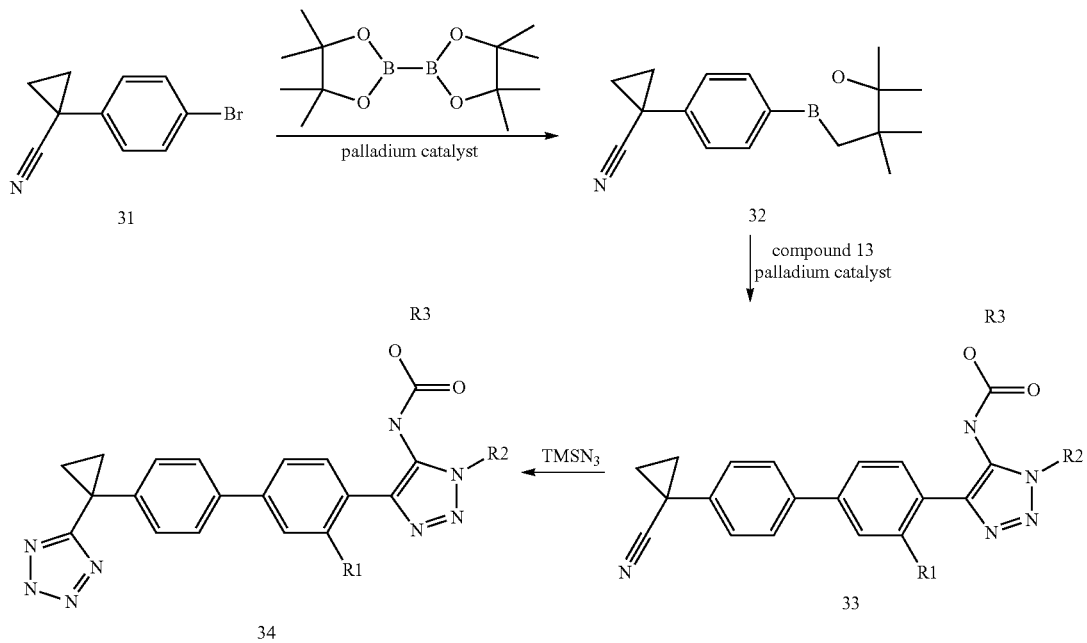

The preparation of a tetrazole analog is described in Scheme 7. Conversion of aryl bromide 31 to the boronate 32 can be accomplished with bis(pinacolato)diboron in the presence of palladium catalyst. Coupling of compound 32 with compound 13 under Suzuki coupling conditions can provide compound 33, which can be converted to a tetrazole 34 by reacting with azidotrimethyl-silane.

EXAMPLES

Although certain exemplary embodiments are depicted and described herein, the compounds of the present invention can be prepared using appropriate starting materials according to the methods described generally herein and/or by methods available to one of ordinary skill in the art.

Definition of abbreviations: DPPA: diphenylphosphorylazide; DPPF: 1,1'-bis(diphenylphosphino)ferrocene; S-Phos: dicyclohexyl(2',6'-dimethoxy[1,1'-biphenyl]-2-yl)-phosphine; X-Phos: dicyclohexyl[2',4',6'-tris(1-methylethyl)[1,1'-biphenyl]-2-yl]-phosphine; DBA: dibenzylidineacetone; DMF: dimethylformamide; LiHMDS: lithium bis(trimethylsilyl)amide; TEA: triethylamine; DCM: dichloromethane; THF: tetrahydrofuran; TLC: thin layer chromatography.

Example 1

[5-(4-Bromo-phenyl)-3-methyl-3H-[1,2,3]triazol-4-yl]-carbamic acid (R)-1-phenyl-ethyl ester

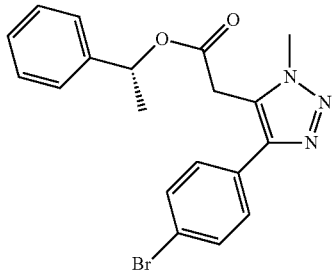 [SMILES: C[C@@H](OC(=O)Cc1c(-c2ccc(Br)cc2)nnn1C)c1ccccc1]

Step 1: preparation of (4-bromo-phenyl)-propionic acid ethyl ester

LDA solution (2M) in THF (20.71 mL, 41.436 mmol) was added to a stirred solution of 1-bromo-4-ethynyl-benzene (3 g, 16.57 mmol) in dry THF (40 mL) at −70° C. and stirred for 30 min. Ethyl chloroformate (11.81 mL, 74.58 mmol) was added and the mixture was allowed to warm to ambient temperature. Stirring was continued for 2 h. The mixture was cooled, and quenched with saturated NH$_4$Cl solution. THF was evaporated under reduced pressure and the aqueous layer was extracted with ethyl acetate. The organic layer was dried over Na$_2$SO$_4$, concentrated and purified over normal silica gel column chromatography using EtOAc-hexane as eluting solvent to get (4-bromo-phenyl)-propynoic acid ethyl ester (2.9 g, 69.13% yield) as a light yellow liquid. GC-MS: 253 (M+H); $^1$H-NMR (400 MHz, CDCl$_3$) δ ppm 1.32 (t, J=7.0 Hz, 3H). 4.28 (q, J=7.0 Hz, 2H), 7.43 (d, J=8.4 Hz, 2H), 7.51 (d, J=8.4 Hz, 2H).

Step 2a: Preparation of 5-(4-bromo-phenyl)-3-trimethylsilanylmethyl-3H-[1,2,3]triazole-4-carboxylic acid ethyl ester To a stirred solution of (4-bromo-phenyl)-propynoic acid ethyl ester (2.5 g, 9.881 mmol) in benzene (4 mL), was added trimethylsilylmethyl azide (5.108 g, 39.52 mmol). The reaction mixture was refluxed for 4 h, then cooled to RT and distilled off the solvent under reduced pressure. Crude mass was purified by normal silica gel column chromatography using EtOAc-hexane as eluting solvent to get two major fractions. One fraction is 5-(4-bromo-phenyl)-3-trimethylsilanylmethyl-3H-[1,2,3]triazole-4-carboxylic acid ethyl ester (1.7 g, 45%) as a light yellow liquid. LC-MS: 382 (M+H); $^1$H-NMR (400 MHz, DMSO-d$_6$) δ ppm 0.10 (s, 9H), 1.21 (t, J=7.2 Hz, 3H), 4.31 (m, 4H), 7.66 (s, 4H). The regio-chemistry was confirmed by NOE study.

Step 2b: Preparation of 5-(4-bromo-phenyl)-1-trimethylsilanylmethyl-1H-[1,2,3]triazole-4-carboxylic acid ethyl ester The other major fraction isolated in Step 2a gave 5-(4-bromo-phenyl)-1-trimethylsilanylmethyl-1H-[1,2,3]triazole-4-carboxylic acid ethyl ester (1.8 g, 47.68% yield) as a light yellow liquid. LC-MS: 382 (M+H). $^1$H-NMR (400 MHz, DMSO-d$_6$) δ ppm 0.02 (s, 9H), 1.13 (t, J=7.2 Hz, 3H), 3.76 (s, 2H), 4.16 (q, J=7.2 Hz, 2H), 7.46 (d, J=8.4 Hz, 2H), 7.74 (d, J=8.4 Hz, 2H). The regio-chemistry was confirmed by NOE study.

Step 3a: Preparation of 5-(4-bromo-phenyl)-3-methyl-3H-[1,2,3]triazole-4-carboxylic acid ethyl ester To a stirred solution of 5-(4-bromo-phenyl)-3-trimethylsilanylmethyl-3H-[1,2,3]triazole-4-carboxylic acid ethyl ester (1.9 g, 4.974 mmol) in THF (40 mL), was added water (0.18 mL, 9.948 mmol) and cooled to 0° C. Then TBAF (1M) solution in THF (5.9 mL, 5.9 mmol) was added and the mixture was stirred at 0° C. for 10 min. Volatiles were distilled off and crude mass was purified by normal silica gel column chromatography using EtOAc-hexane as eluting solvent to get 5-(4-bromo-phenyl)-3-methyl-3H-[1,2,3]triazole-4-carboxylic acid ethyl ester (0.7 g, 45.42% yield) as an off white solid. LC-MS: 310 (M+H); $^1$H-NMR (400 MHz, DMSO-d$_6$) δ ppm 1.23 (t, J=7.0 Hz, 3H), 4.27 (s, 3H), 4.31 (q, J=7.0 Hz, 2H), 7.68 (s, 4H). The regio-chemistry was confirmed by NOE study.

Step 3b: Preparation of 5-(4-bromo-phenyl)-1-methyl-1H-[1,2,3]triazole-4-carboxylic acid ethyl ester To a stirred solution of 5-(4-bromo-phenyl)-1-trimethylsilanylmethyl-1H-[1,2,3]triazole-4-carboxylic acid ethyl ester (6.5 g, 17.01 mmol) in THF (100 mL), was added water (0.61 ml, 34.03 mmol) and cooled to 0° C. Then TBAF (1M) solution in THF (20.41 mL, 20.41 mmol) was added to it and the mixture was stirred at 0° C. for 10 min. Volatiles were distilled off and crude mass was purified by normal silica gel column chromatography using EtOAc-hexane as eluting solvent to get 5-(4-bromo-phenyl)-1-methyl-1H-[1,2,3]triazole-4-carboxylic acid ethyl ester (4.7 g, 89.02%) as a white solid. LC-MS: 310 (M+H); $^1$H-NMR (400 MHz, DMSO-d$_6$) δ ppm 1.14 (t, J=7.0 Hz, 3H), 3.91 (s, 3H), 4.18 (q, J=7.0 Hz, 2H), 7.51 (d, J=8.4 Hz, 2H), 7.75 (d, J=8.4 Hz, 2H). The regio-chemistry was confirmed by NOE study.

Step 4a: Preparation of 5-(4-bromo-phenyl)-3-methyl-3H-[1,2,3]triazole-4-carboxylic acid 5-(4-Bromo-phenyl)-3-methyl-3H-[1,2,3]triazole-4-carboxylic acid ethyl ester (1.2 g, 3.87 mmol) was dissolved in THF (15 mL) and lithium hydroxide solution (0.5 N, 10 mL) was added. The mixture was stirred at room temperature for 3 hrs. TLC indicated complete consumption of the starting material. The mixture was concentrated and the residue was dissolved in water (20 mL) and filtered. The filtrate was acidified with 2N hydrochloric acid (3 mL). The white solid was filtered and dried to give 5-(4-bromo-phenyl)-3-methyl-3H-[1,2,3]triazole-4-carboxylic acid as a white solid (1.03 g, 94.4% yield). m.p. 209-210° C.; LC-MS calcd for $C_{10}H_8BrN_3O_2$ (m/e) 283.0, obsd 284.0 (M+H); $^1$H-NMR (400 MHz, DMSO-$d_6$) δ ppm 4.26 (s, 3H), 7.66-7.72 (m, 4H), 14.20 (br s, 1H).

Step 4b: Preparation of 5-(4-bromo-phenyl)-1-methyl-1H-[1,2,3]triazole-4-carboxylic acid Ethyl 5-(4-bromophenyl)-1-methyl-1H-[1,2,3]triazole-4-carboxylate (from step 3b, 2.0 g, 6.45 mmol) was dissolved in 30 mL of THF and 0.5N lithium hydroxide solution (15 mL) was added. The mixture was stirred at room temperature for 10 hrs and solvents were evaporated. The residue was dissolved in water (30 mL) and filtered. The filtrate was treated with hydrochloric acid (2N, 4 mL). The white solid was filtered and dried to give 5-(4-bromo-phenyl)-1-methyl-1H-[1,2,3]triazole-4-carboxylic acid (1.82 g, 100% yield). LC-MS calcd for $C_{10}H_8BrN_3O_2$ (m/e) 283.0, obsd 282.0 (M–H); $^1$H-NMR (400 MHz, DMSO-$d_6$) δ ppm 3.89 (s, 3H), 7.50 (d, J=8.4 Hz, 2H), 7.75 (d, J=8.4 Hz, 2H), 12.95 (br s, 1H).

Step 5: Preparation of [5-(4-Bromo-phenyl)-3-methyl-3H-[1,2,3]triazol-4-yl]-carbamic acid (R)-1-phenyl-ethyl ester 5-(4-bromophenyl)-3-methyl-3H-[1,2,3]triazole-4-carboxylic acid (500 mg, 1.77 mmol), (R)-1-phenylethanol (260 mg, 2.13 mmol), DPPA (537 mg, 1.95 mmol), and TEA (179 mg, 1.7 mmol) were combined in toluene (10 mL). The mixture was stirred at 90° C. for 2 hrs and solvents were evaporated. The residue was extracted with ethyl acetate and water. The organic layer was washed with sodium bicarbonate solution and dried. Solvents were evaporated and the residue was purified by ISCO flash column chromatography (80 silica gel, ethyl acetate in hexanes 0% to 50%) to give [5-(4-bromo-phenyl)-3-methyl-3H-[1,2,3]triazol-4-yl]-carbamic acid (R)-1-phenyl-ethyl ester as an amorphous powder (440 mg, 61.9% yield). LC-MS calcd for $C_{18}H_{17}BrN_4O_2$ (m/e) 402, obsd 402.9 (M+H); $^1$H-NMR (400 MHz, DMSO-$d_6$) δ ppm 1.55 (br, 3H)), 3.83 (s, 3H), 5.76 (br s, 1H), 7.20-7.50 (m, 5H), 7.57-7.70 (m, 4H), 9.95 (br s, 1H).

Example 2

1-{4'-[1-Methyl-5-((R)-1-phenyl-ethoxycarbonylamino)-1H-[1,2,3]triazol-4-yl]-biphenyl-4-yl}-cyclopropanecarboxylic acid

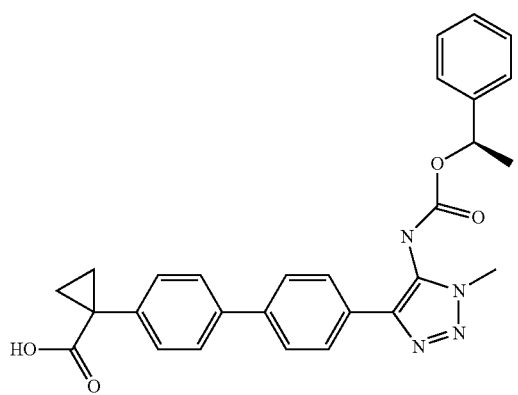 [SMILES: C[C@@H](OC(=O)Nc1c(-c2ccc(-c3ccc(C4(C(=O)O)CC4)cc3)cc2)nnn1C)c1ccccc1]

[5-(4-Bromo-phenyl)-3-methyl-3H-[1,2,3]triazol-4-yl]-carbamic acid (R)-1-phenyl-ethyl ester (from Example 1, 566 mg, 1.41 mmol), methyl 1-(4-(4,4,5,5-tetramethyl-1,3,2-dioxaborolan-2-yl)phenyl)cyclopropanecarboxylate (511 mg, 1.69 mmol), X-Phos (134 mg, 0.28 mmol), palladium acetate (31.7 mg, 0.14 mmol) and potassium phosphate (898 mg, 4.23 mmol) were combined in toluene (12 mL) and degassed water (3 mL) was added. The mixture was degassed and sealed. The mixture was stirred at 95° C. for 3 hrs and cooled to room temperature. The mixture was extracted with ethyl acetate and water. The organic layer was washed with brine and dried. Solvents were evaporated and the residue was purified by flash column chromatography (40 g silica gel, ethyl acetate in hexanes 10% to 70% in 15 minutes) to give 1-{4'-[1-methyl-5-((R)-1-phenyl-ethoxycarbonylamino)-1H-[1,2,3]triazol-4-yl]-biphenyl-4-yl}-cyclopropanecarboxylic acid methyl ester as a pale yellow solid (370 mg, 52.8% yield). LC/MS calcd for $C_{29}H_{28}N_4O_4$ (m/e) 496.0, obsd 497.0 (M+H); $^1$H-NMR (400 MHz, CDCl$_3$) δ ppm 1.25 (m, 3H), 1.66 (m, 4H), 3.67 (s, 3H), 3.93 (s, 3H), 5.91 (m, 1H), 6.44 (br, 1H), 7.29-7.40 (m, 5H), 7.44 (d, J=8.1 Hz, 2H), 7.57 (d, J=8.3 Hz, 2H), 7.61 (d, J=8.3 Hz, 2H), 7.78 (br d, J=6.6 Hz, 2H). 1-{4'-[1-Methyl-5-((R)-1-phenyl-ethoxycarbonylamino)-1H-[1,2,3]triazol-4-yl]-biphenyl-4-yl}-cyclopropanecarboxylic acid methyl ester (50 mg) was dissolved in 1 mL of THF and 1 mL of ethanol. To this mixture was added 1N sodium hydroxide solution (1 mL). The clear solution was stirred at room temperature for 12 hrs. Solvents were evaporated and the residue was treated with 2N hydrochloric acid (1.4 mL). The solid was filtered and rinsed with water, dried in the air, to give 1-{4'-[1-methyl-5-((R)-1-phenyl-ethoxycarbonylamino)-1H-[1,2,3]triazol-4-yl]-biphenyl-4-yl}-cyclopropanecarboxylic acid (47.5 mg, 97.8% yield). LC/MS calcd for $C_{28}H_{26}N_4O_4$ (m/e) 482.0, obsd 483.0 (M+H); $^1$H-NMR (400 MHz, DMSO-$d_6$) δ ppm 1.14-1.24 (m, 3H), 1.49 (m, 2H), 1.59 (m, 2H), 3.86 (s, 3H), 5.80 (m, 1H), 7.28-7.50 (m, 7H), 7.63 (d, J=8.1 Hz, 2H), 7.71 (m, 2H), 7.80 (d, J=7.6 Hz, 2H), 9.95 and 9.62 (br s, 1H), 12.35 (s, 1H).

Example 3

{4'-[1-Methyl-5-((R)-1-phenyl-ethoxycarbonylamino)-1H-[1,2,3]triazol-4-yl]-biphenyl-4-yl}-acetic acid

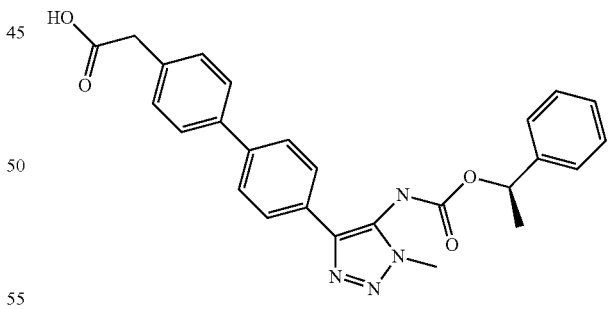

[5-(4-Bromo-phenyl)-3-methyl-3H-[1,2,3]triazol-4-yl]-carbamic acid (R)-1-phenyl-ethyl ester (from Example 1, 120 mg, 0.30 mmol), ethyl 2-(4-(4,4,5,5-tetramethyl-1,3,2-dioxaborolan-2-yl)-phenyl)acetate (130 mg, 0.45 mmol), X-PHOS (43 mg, 0.09 mmol), palladium acetate (10 mg, 0.045 mmol) and potassium phosphate (190 mg, 0.90 mmol) were combined in 5 mL of toluene. Deionized water (1 mL) was added and the mixture was degassed with argon for 2 minutes. The mixture was sealed and stirred at 100° C. for 2 hrs. The mixture was extracted with ethyl acetate and water, washed with brine and dried. Solvents were evaporated and the residue was purified by ISCO flash column chromatography (12 g silica gel, 0% to 70% ethyl acetate in hexanes) to give {4'-[1-methyl-5-((R)-1-phenyl-ethoxycarbonylamino)-1H-[1,2,3]triazol-4-yl]-biphenyl-4-yl}-acetic acid ethyl ester as an amorphous powder (70 mg, 48.3% yield). LC/MS calcd for $C_{28}H_{28}N_4O_4$ (m/e) 484.0, obsd 485.1 (M+H); $^1$H-NMR (400 MHz, CDCl$_3$) δ ppm 1.31 (t, J=7.2 Hz, 3H), 1.53-1.76 (m, 3H), 3.69 (s, 2H), 3.95 (s, 3H), 4.21 (q, J=7.2 Hz, 2H), 5.93 (m, 1H), 6.40 (br s, 1H), 7.31-7.49 (m, 7H), 7.56-7.66 (m, 4H), 7.80 (d, J-6.8 Hz, 2H). {4'-[1-Methyl-5-((R)-1-phenyl-ethoxycarbonylamino)-1H-[1,2,3]triazol-4-yl]-biphenyl-4-yl}-acetic acid ethyl ester (60 mg, 0.124 mmol) was dissolved in 3 mL of THF and lithium hydroxide solution (0.5 N, 1.0 mL) was added. The mixture was stirred at room temperature for 3 hrs. TLC indicated complete consumption of the starting material. The mixture was concentrated and dissolved in water (8 mL). The clear solution was treated with hydrochloric acid (1N, 0.6 mL). The mixture was filtered and the white solid was dried to give {4'-[1-methyl-5-((R)-1-phenyl-ethoxycarbonylamino)-1H-[1,2,3]triazol-4-yl]-biphenyl-4-yl}-acetic acid (51 mg, 90.2% yield). LC/MS calcd for $C_{26}H_{24}N_4O_4$ (m/e) 456.0, obsd 457.0 (M+H); $^1$H-NMR (400 MHz, DMSO-d$_6$) ppm 1.12-1.32 (m, 0.6H), 1.59 (br, 2.4H), 3.64 (s, 2H), 3.89 (s, 3H), 5.80 (br m, 1H), 6.96-7.54 (m, 7H), 7.61-7.74 (m, 4H), 7.80 (d, J=7.6 Hz, 2H), 9.54 and 9.95 (br s, 1H), 12.38 (br s, 1H).

Example 4

1-(4'-{1-Methyl-5-[1-(3-trifluoromethyl-phenyl)-ethoxycarbonylamino]-1H-[1,2,3]triazol-4-yl}-biphenyl-4-yl)-cyclopropanecarboxylic acid

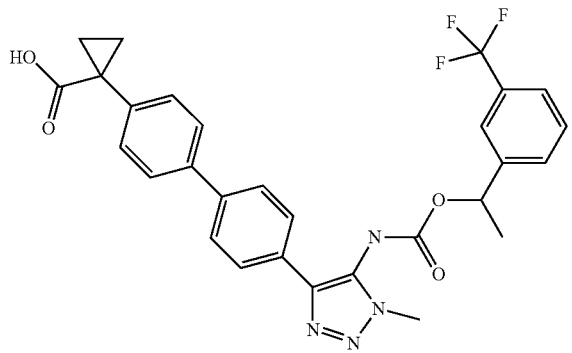 [SMILES: CC(OC(=O)Nc1c(-c2ccc(-c3ccc(C4(C(=O)O)CC4)cc3)cc2)nnn1C)c1cccc(C(F)(F)F)c1]

5-(4-Bromophenyl)-3-methyl-3H-[1,2,3]triazole-4-carboxylic acid (from step 4a in Example 1, 517 mg, 1.83 mmol) was suspended in 10 mL of toluene. Triethylamine (0.27 mL) was added followed by DPPA (530 mg, 1.92 mmol) in toluene (2 mL). The mixture was stirred for 10 minutes. 3-Trifluoromethylphenylethanol (383 mg, 2.02 mmol) in toluene (2 mL) was added. The mixture was stirred at 85° C. for 3 hrs. The mixture was extracted with ethyl acetate and water. The organic layer was washed with brine and dried. Solvents were evaporated and the residue was purified by ISCO flash column chromatography (0% to 50% ethyl acetate in hexanes, 40 g silica gel) to give [5-(4-bromo-phenyl)-3-methyl-3H-[1,2,3]triazol-4-yl]-carbamic acid 1-(3-trifluoromethyl-phenyl)-ethyl ester as an amorphous fluffy white powder (700 mg, 81.4% yield). LC/MS calcd for $C_{19}H_{16}BrF_3N_4O_2$ (m/e) 468.0, obsd 468.9 (M+H); $^1$H-NMR (400 MHz, DMSO-d$_6$) δ ppm 1.35-1.70 (br, 3H), 3.85 (s, 3H), 5.85 (br, 1H), 7.30-7.90 (m, 8H), 10.01 (br s, 1H).

[5-(4-Bromo-phenyl)-3-methyl-3H-[1,2,3]triazol-4-yl]-carbamic acid 1-(3-trifluoromethyl-phenyl)-ethyl ester (680 mg, 1.45 mmol), methyl 1-(4-(4,4,5,5-tetramethyl-1,3,2-dioxaborolan-2-yl)phenyl)cyclopropanecarboxylate (525 mg, 1.74 mmol), X-Phos (138 mg, 0.29 mmol), palladium acetate (33 mg, 0.14 mmol) and potassium phosphate tribasic (923 mg, 4.35 mmol) were mixed in toluene (10 mL). Degassed water (2 mL) was added and the mixture was degassed with argon and then sealed. The mixture was stirred at 95° C. for 5 hrs until all starting material was consumed. The mixture was extracted with ethyl acetate and water. The organic layer was washed with brine and dried. Solvents were evaporated and the residue was purified by flash column chromatography (ethyl acetate in hexanes 5% to 70% in 15 minutes, 40 g silica gel) to give an amorphous white fluffy material as 1-(4'-{1-methyl-5-[1-(3-trifluoromethyl-phenyl)-ethoxycarbonylamino]-1H-[1,2,3]triazol-4-yl}-biphenyl-4-yl)-cyclopropanecarboxylic acid methyl ester (436 mg, 53.3% yield). LC/MS calcd for $C_{30}H_{27}F_3N_4O_4$ (m/e) 564.0, obsd 565.0 (M+H); $^1$H-NMR (400 MHz, DMSO-d$_6$) δ ppm 1.18-1.35 (m, 2.6H), 1.48-1.55 (m, 2H), 1.60 (br d, J=3.8 Hz, 2.4H), 3.57 (s, 3H), 3.86 (s, 3H), 5.80-5.90 (br m, 1H), 7.44 (d, J=8.3 Hz, 2.5H), 7.63 (d, J=8.1 Hz, 2.5H), 7.69 (br d, J=7.3 Hz, 3.5H), 7.80 (d, J=7.3 Hz, 3.5H), 9.65 and 10.06 (br s, 1H).

1-(4'-{1-Methyl-5-[1-(3-trifluoromethyl-phenyl)-ethoxycarbonylamino]-1H-[1,2,3]triazol-4-yl}-biphenyl-4-yl)-cyclopropanecarboxylic acid methyl ester (410 mg, 0.726 mmol) was dissolved 4 mL of THF and 4 mL of ethanol. To this stirred solution was added 1N sodium hydroxide solution (8 mL). The mixture was stirred at room temperature overnight. TLC indicated complete consumption of the starting material. The mixture was concentrated and the residue was dissolved in 15 mL of water. Dilute hydrochloric acid (1N, 9 mL) was added. The white solid was filtered and dried in the air to give 1-(4'-{1-methyl-5-[1-(3-trifluoromethyl-phenyl)-ethoxycarbonylamino]-1H-[1,2,3]triazol-4-yl}-biphenyl-4-yl)-cyclopropanecarboxylic acid (400 mg, 100% yield). LC/MS calcd for $C_{29}H_{25}F_3N_4O_4$ (m/e) 550.0, obsd 551.0 (M+H); $^1$H-NMR (400 MHz, DMSO-d$_6$) δ ppm 1.13-1.29 (m, 2.6H), 1.44-1.52 (m, 2H), 1.60 (br d, 2.4H), 3.86 (s, 3H), 5.75-5.95 (br m, 1H), 7.43 (d, J=8.1 Hz, 2.5H), 7.61 (d, J=8.1 Hz, 2.5H), 7.69 (br m, 3.5H), 7.79 (d, J=7.6 Hz, 3.5H), 9.65 and 10.05 (br s, 1H), 12.35 (s, 1H).

Example 5

1-(4'-{1-Methyl-5-[(S)-1-(3-trifluoromethyl-phenyl)-ethoxycarbonylamino]-1H-[1,2,3]triazol-4-yl}-biphenyl-4-yl)-cyclopropanecarboxylic acid

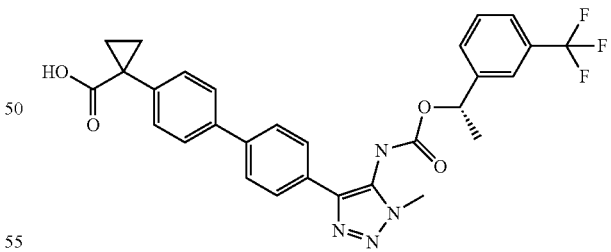

1-(4'-(1-Methyl-5-((1-(3-(trifluoromethyl)-phenyl)-ethoxy)carbonylamino)-1H-[1,2,3]triazol-4-yl)-biphenyl-4-yl)cyclopropanecarboxylic acid (370 mg, racemic, from Example 4) was separated by super critical fluid chromatography on Waters/Berger Multigram II using a Whelk-O1 (R,R)-column (3×25 cm) eluted with 50% isopropanol in CO$_2$ at 70 mL/min (detection at 220 nM, 100 Bar backpressure, and 35° C. oven). The first fraction gave 1-(4'-{1-methyl-5-[(S)-1-(3-trifluoromethyl-phenyl)-ethoxycarbonylamino]-1H-[1,2,3]triazol-4-yl}-biphenyl-4-yl)-cyclopropanecarboxylic acid (158 mg) as a white solid. LC/MS calcd for $C_{29}H_{25}F_3N_4O_4$ (m/e) 550.0, obsd 551.0

(M+H); $^1$H-NMR (400 MHz, DMSO-d$_6$) δ ppm 1.13-1.29 (m, 2.6H), 1.44-1.52 (m, 2H), 1.60 (br d, 2.4H), 3.86 (s, 3H), 5.75-5.95 (br m, 1H), 7.43 (d, J=8.1 Hz, 2.5H), 7.61 (d, J=8.1 Hz, 2.5H), 7.69 (br m, 3.5H), 7.79 (d, J=7.6 Hz, 3.5H), 9.65 and 10.05 (br s, 1H), 12.35 (s, 1H).

Example 6

1-(4'-{1-Methyl-5-[(R)-1-(3-trifluoromethyl-phenyl)-ethoxycarbonylamino]-1H-[1,2,3]triazol-4-yl}-biphenyl-4-yl)-cyclopropanecarboxylic acid

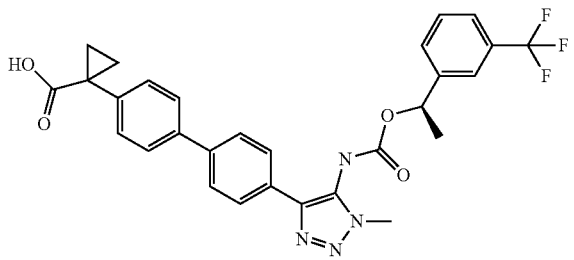 [SMILES: C[C@@H](OC(=O)Nc1c(-c2ccc(-c3ccc(C4(C(=O)O)CC4)cc3)cc2)nnn1C)c1cccc(C(F)(F)F)c1]

1-(4'-(1-Methyl-5-((1-(3-(trifluoromethyl)-phenyl)-ethoxy)carbonylamino)-1H-[1,2,3]triazol-4-yl)-biphenyl-4-yl)cyclopropanecarboxylic acid (370 mg, racemic, from Example 4) was separated by super critical fluid chromatography on Waters/Berger Multigram II using a Whelk-O1 (R,R)-column (3×25 cm) eluted with 50% isopropanol in CO$_2$ at 70 mL/min (detection at 220 nM, 100 Bar backpressure, and 35° C. oven). The second fraction gave 1-(4'-{1-methyl-5-[(R)-1-(3-trifluoromethyl-phenyl)-ethoxycarbonylamino]-1H-[1,2,3]triazol-4-yl}-biphenyl-4-yl)-cyclopropanecarboxylic acid (159 mg) as a white solid. LC/MS calcd for C$_{29}$H$_{25}$F$_3$N$_4$O$_4$ (m/e) 550.0, obsd 551.0 (M+H); $^1$H-NMR (400 MHz, DMSO-d$_6$) ppm 1.13-1.29 (m, 2.6H), 1.44-1.52 (m, 2H), 1.60 (br d, 2.4H), 3.86 (s, 3H), 5.75-5.95 (br m, 1H), 7.43 (d, J=8.1 Hz, 2.5H), 7.61 (d, J=8.1 Hz, 2.5H), 7.69 (br m, 3.5H), 7.79 (d, J=7.6 Hz, 3.5H), 9.65 and 10.05 (br s, 1H), 12.35 (s, 1H). The absolute stereo chemistry was also confirmed by using (R)-1-(3-trifluoromethylphenyl)-ethanol.

Example 7

1-{4'-[5-((R)-1,2-Dimethyl-propoxycarbonylamino)-1-methyl-1H-[1,2,3]triazol-4-yl]biphenyl-4-yl}-cyclopropanecarboxylic acid

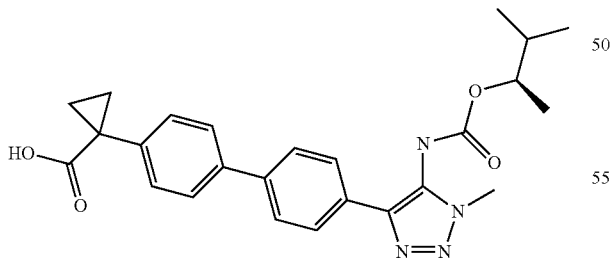

5-(4-Bromophenyl)-3-methyl-3H-[1,2,3]triazole-4-carboxylic acid (330 mg, 1.17 mmol), (R)-3-methylbutan-2-ol (113 mg, 1.29 mmol), DPPA (338 mg, 1.23 mmol) and TEA (0.18 mL) were combined in toluene (15 mL). The solution was stirred at 90° C. for 3 hrs. Solvents were evaporated and the residue was extracted with water. The organic layer was dried and concentrated. The residue was purified by ISCO flash column chromatography (24 g silica gel, 0% to 60% ethyl acetate in hexanes) to give a pale yellow amorphous material as (R)-3-methylbutan-2-yl 4-(4-bromophenyl)-1-methyl-1H-1,2,3-triazol-5-ylcarbamate (297 mg, 69.1% yield). LC/MS calcd for C$_{15}$H$_{19}$BrN$_4$O$_2$ (m/e) 366.0, obsd 366.9 (M+H).

(R)-3-Methylbutan-2-yl 4-(4-bromophenyl)-1-methyl-1H-1,2,3-triazol-5-ylcarbamate (101.4 mg. 0.28 mmol), methyl 1-(4-(4,4,5,5-tetramethyl-1,3,2-dioxaborolan-2-yl)phenyl)cyclopropanecarboxylate (108 mg, 0.36 mmol), X-Phos (39.5 mg, 0.083 mmol), palladium acetate (9.3 mg, 0.041 mmol), and potassium phosphate tribasic (176 mg, 0.83 mmol) were combined in toluene (6 mL). To this mixture was added degassed water (1.5 mL) and the mixture was stirred at 95° C. for 2 hrs until it became black. LC/MS indicated no more starting material. The mixture was extracted with ethyl acetate and water. The organic layer was washed with brine and dried. Solvents were evaporated and the residue was purified by ISCO flash column chromatography (12 g silica gel, 5% to 65% ethyl acetate in hexanes) to give a pale yellow solid as 1-{4'-[5-((R)-1,2-dimethyl-propoxycarbonylamino)-1-methyl-1H-[1,2,3]triazol-4-yl]-biphenyl-4-yl}-cyclopropanecarboxylic acid methyl ester (97.8 mg, 76.6% yield). LC/MS calcd for C$_{26}$H$_{30}$N$_4$O$_4$ (m/e) 462, obsd 463.2 (M+H).

1-{4'-[5-((R)-1,2-Dimethyl-propoxycarbonylamino)-1-methyl-1H-[1,2,3]triazol-4-yl]-biphenyl-4-yl}-cyclopropanecarboxylic acid methyl ester (97 mg) was dissolved in 2 mL of THF and 2 mL of ethanol. To this clear solution was added 1N NaOH solution 2 mL. The clear solution was stirred at room temperature overnight. Solvents were evaporated and the residue was dissolved in water (12 mL). The solution was filtered. The filtrate was treated with hydrochloric acid (1N, 2.5 mL). The white precipitate was filtered and dried in air to provide 1-{4'-[5-((R)-1,2-dimethyl-propoxycarbonylamino)-1-methyl-1H-[1,2,3]triazol-4-yl]-biphenyl-4-yl}-cyclopropanecarboxylic acid as a pale yellow solid (84 mg, 89.3% yield). LC/MS calcd for C$_{25}$H$_{28}$N$_4$O$_4$ (m/e) 448.0, obsd 449.2 (M+H); $^1$H-NMR (300 MHz, DMSO-d$_6$) δ ppm 0.52 (br, 1H), 0.88 (br, 5H), 1.04-1.25 (m, 5H), 1.35-1.43 (m, 2H), 1.62-1.85 (br, 1H), 3.80 (s, 3H), 4.55 (br, 1H), 7.35 (d, J=8.3 Hz, 2H), 7.57 (d, J=8.3 Hz, 2H), 7.68 (d, J=8.3 Hz, 2H), 7.78 (d, J=8.3 Hz, 2H), 9.34 and 9.67 (br s, 1H), 12.30 (br s, 1H).

Example 8

1-{4'-[3-Methyl-5-((R)-1-phenyl-ethoxycarbonylamino)-3H-[1,2,3]triazol-4-yl]-biphenyl-4-yl}-cyclopropanecarboxylic acid

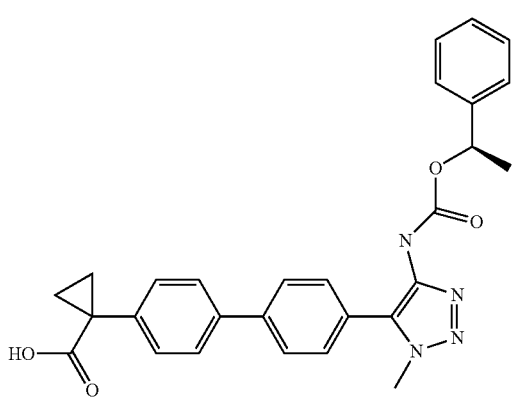 [SMILES: C[C@@H](OC(=O)Nc1nnn(C)c1-c1ccc(-c2ccc(C3(C(=O)O)CC3)cc2)cc1)c1ccccc1]

This compound was prepared using the same method as described for the preparation of 1-{4'-[1-methyl-5-((R)-1- phenyl-ethoxycarbonylamino)-1H-[1,2,3]triazol-4-yl]-biphenyl-4-yl}-cyclopropanecarboxylic acid in Example 2, except that 5-(4-bromo-phenyl)-1-methyl-1H-[1,2,3]triazole-4-carboxylic acid (from step 4b in Example 1) was used. LC/MS calcd for $C_{28}H_{26}N_4O_4$ (m/e) 482.0, obsd 483.0 (M+H); $^1$H-NMR (400 MHz, DMSO-$d_6$) δ ppm 1.15-1.30 (m, 2.4H), 1.32-1.62 (m, 4.6H), 4.05 (s, 3H), 5.69 (br m, 1H), 7.20-7.40 (br m, 5H), 7.46 (d, J=8.1 Hz, 2H), 7.59 (d, J=−8.1 Hz, 2H), 7.66 (d, J=8.1 Hz, 2H), 7.77 (d, J=7.6 Hz, 2H), 9.34 (br s, 1H), 12.39 (s, 1H).

Example 9

(R)-1-(4'-(1-Methyl-5-((1-phenylethoxy)carbonylamino)-1H-1,2,3-triazol-4-yl)biphenyl-3-yl)cyclopropanecarboxylic acid

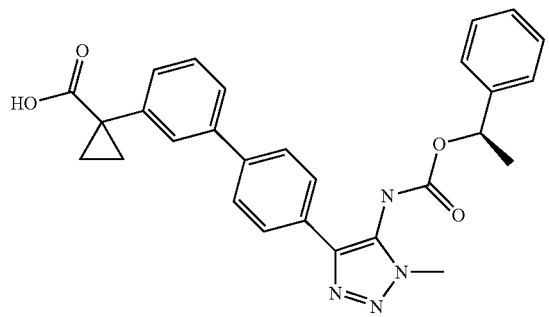 [SMILES: C[C@@H](OC(=O)Nc1c(-c2ccc(-c3cccc(C4(C(=O)O)CC4)c3)cc2)nnn1C)c1ccccc1]

A 350 ml, sealed cap vessel was charged with 1-(3-bromophenyl)cyclopropanecarboxylic acid ethyl ester (3.56 g, 13.2 mmol), 4,4,4',4',5,5,5',5'-octamethyl-2,2'-bi(1,3,2-dioxaborolane) (4.03 g, 15.9 mmol), and potassium acetate (2.6 g, 26.5 mmol) and then 1,4-Dioxane (40 mL) was added to give a white suspension. Then, the nitrogen gas was bubbled through the reaction mixture for 10 minutes before the addition of [1,1'-bis(diphenylphosphino)ferrocene]dichloropalladium(II) (484 mg, 0.66 mmol) at room temperature. The flask was sealed with a cap and the brown reaction mixture was heated in an oil bath at 80° C. for 5 h. Then, it was cooled to room temperature and poured into a solution of water (100 mL) and brine (100 mL) and the organic compound was extracted into ethyl acetate (2×150 mL). The combined extracts were washed with brine solution and dried over anhydrous MgSO$_4$. Filtration and concentration gave the crude black oil which was purified using an ISCO (120 g) column chromatography eluting with 0-60% ethyl acetate in hexanes. The desired fractions were combined and the solvent was removed under vacuum to obtain 1-(3-(4,4,5,5-tetramethyl-1,3,2-dioxaborolan-2-yl)phenyl)cyclopropane carboxylic acid ethyl ester as viscous oil (2.55 g, 61% yield). LC/MS calcd. for $C_{18}H_{25}BO_4$ (m/e) 316.0, obsd. 317.2 (M+H, ES+).

To a mixture of (R)-1-phenylethyl 4-(4-bromophenyl)-1-methyl-1H-1,2,3-triazol-5-ylcarbamate (120 mg, 0.3 mmol), ethyl 1-(3-(4,4,5,5-tetramethyl-1,3,2-dioxaborolan-2-yl)phenyl)cyclopropanecarboxylic acid ethyl ester (142 mg, 0.449 mmol), palladium(II) acetate (10.1 mg, 0.05 mmol), 2-dicyclohexylphosphino-2',6'-dimethoxybiphenyl (36.8 mg, 0.1 mmol), and potassium phosphate tribasic (190 mg, 0.9 mmol) in a vial were added toluene (2.25 mL) and water (0.5 mL) at room temperature under nitrogen atmosphere. The resulting light brown suspension was disconnected from the nitrogen line and the reaction mixture was heated to 105° C. and the progress of the reaction was followed by TLC analysis and it was completed after 1 h at this temperature. Then, it was cooled to room temperature and diluted with water and ethyl acetate. The two layers were separated and the aqueous layer was extracted with ethyl acetate (50 mL). The combined organic layer was washed with brine solution and dried over anhydrous MgSO$_4$. Filtration and concentration gave the crude compound which was purified using an ISCO (40 g) column chromatography eluting with 0-70% ethyl acetate in hexanes. The desired fractions were combined and the solvent was removed under vacuum to obtain (R)-1-(4'-(1-methyl-5-((1-phenylethoxy)-carbonylamino)-1H-1,2,3-triazol-4-yl)biphenyl-3-yl)cyclopropanecarboxylic acid ethyl ester as a white solid (94 mg, 61% yield). LC/MS calcd. for $C_{30}H_{30}N_4O_4$ (m/e) 510.0, obsd. 511.1 (M+H, ES+).

To a solution of (R)-1-(4'-(1-methyl-5-((1-phenylethoxy)carbonylamino)-1H-1,2,3-triazol-4-yl)biphenyl-3-yl)cyclopropanecarboxylic acid ethyl ester (90 mg, 0.176 mmol) in THF (5 mL) and ethanol (5 mL) was added an excess of sodium hydroxide (1.76 mL, 1.76 mmol, 1.0 M) in water at room temperature. The resulting colorless solution was stirred for 20 h at which time LCMS analysis indicated the absence of starting material. Then, the solvent was removed under vacuum and the basic aqueous layer was neutralized with 1.0 N HCl. The resulting white solids were collected by filtration and washed with water and hexanes. After air drying, 75 mg (88% yield) of the (R)-1-(4'-(1-methyl-5-((1-phenylethoxy)carbonylamino)-1H-1,2,3-triazol-4-yl)biphenyl-3-yl)cyclopropanecarboxylic acid was isolated as a white solid. LC/MS calcd. for $C_{28}H_{26}N_4O_4$ (m/e) 482.0, obsd. 483.1 (M+H, ES+).

Example 10

1-{3'-Fluoro-4'-[1-methyl-5-((R)-1-phenyl-ethoxycarbonylamino)-1H-[1,2,3]triazole-4-yl]-biphenyl-4-yl}-cyclopropanecarboxylic acid methyl ester

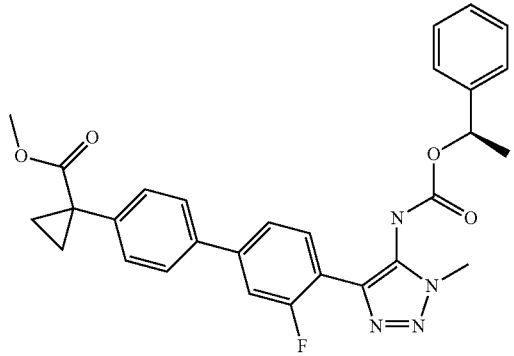 [SMILES: COC(=O)C1(c2ccc(-c3ccc(-c4nnn(C)c4NC(=O)O[C@H](C)c4ccccc4)c(F)c3)cc2)CC1]

Step 1: Preparation of (4-bromo-2-fluoro-phenyl)-propynoic acid ethyl ester

In a 100 mL round-bottomed flask, 4-bromo-1-ethynyl-2-fluorobenzene (2.0 g, 10.0 mmol) was combined with THF (28 ml) to give a brown solution. The solution was cooled to −78° C. and 1.5M LDA in cyclohexane (16.4 mL, 24.6 mmol, Eq: 2.45) was added via syringe. The reaction was stirred at −78° C. for 20 mins, ethyl chloroformate (5.42 g, 4.8 mL, 50.0 mmol, Eq: 4.97) was added at −78° C. and the reaction was stirred at room temp for 2 h under argon. The reaction was quenched with saturated NH₄Cl and diluted with EtOAc. The aqueous layer was back-extracted with EtOAc. The organic layers were combined, washed with 1 M HCl (2×50 mL), H₂O (1×50 mL), saturated NaHCO₃ (1×50 mL) and brine (1×25 mL), dried over Na₂SO₄ and concentrated in vacuo to a dark red oil. The crude material was purified by flash chromatography (silica gel, 220 g, 0% to 20% EtOAc in heptane) to afford a pure fraction (4.49 g, 46%) of the desired product as an off white solid. The less pure fraction was stripped and the residue was recrystallized from EtOAc/hexane to afford an additional 1.64 g (17%) of the desired product as a pink powder. $^1$H NMR (CDCl₃) δ ppm 7.40-7.53 (m, 1H), 7.28-7.39 (m, 2H), 4.28 (q, J=7.0 Hz, 2H), 1.32 (t, J=7.0 Hz, 3H).

Step 2: Preparation of 5-(4-bromo-2-fluoro-phenyl)-3-trimethylsilanylmethyl-3H-[1,2,3]triazole-4-carboxylic acid ethyl ester In a 50 mL pear-shaped flask, ethyl 3-(4-bromo-2-fluorophenyl)propiolate (1.27 g, 4.68 mmol) and (azidomethyl)trimethylsilane (2.42 g, 2.78 mL, 18.7 mmol, Eq: 4) were combined with benzene (3.5 mL) to give a light yellow solution. The reaction mixture was heated to 90° C. and stirred for 4 h. The reaction mixture was concentrated in vacuo. The crude material was purified by flash chromatography (silica gel, 80 g, 0% to 20% EtOAc in heptane) to afford 616 mg (33%) of the desired less polar regio-isomer as a white solid. (M+H)⁺=400.0/402.0 m/e.
$^1$H NMR (DMSO-d₆) δ ppm 7.68-7.75 (m, 1H), 7.49-7.64 (m, 2H), 4.30-4.38 (m, 2H), 4.23 (q, J=7.2 Hz, 2H), 1.11 (t, J=7.1 Hz, 3H), 0.06-0.12 (m, 9H).

Step 3: Preparation of 5-(4-bromo-2-fluoro-phenyl)-3-methyl-3H-[1,2,3]triazole-4-carboxylic acid ethyl ester In a 250 mL round-bottomed flask, 5-(4-bromo-2-fluorophenyl)-3-trimethylsilanylmethyl-3H-[1,2,3]triazole-4-carboxylic acid ethyl ester (616 mg, 1.54 mmol) and water (55.4 mg, 55.4 μL, 3.08 mmol, Eq: 2) were combined with tetrahydrofuran (13 mL) to give a light yellow solution. The reaction was cooled to 0° C. and 1M TBAF in THF (1.85 ml, 1.85 mmol, Eq: 1.2) was added. The reaction was stirred for 20 mins at 0° C. then concentrated in vacuo. The crude material was purified by flash chromatography (silica gel, 40 g, 0% to 20% EtOAc in heptane) to afford 291 mg (58%) of the desired product as a white solid. (M+H)⁺=327.9/329.9 m/e; $^1$H NMR (DMSO-d₆) δ ppm 7.73 (dq, J=9.9, 0.7 Hz, 1H), 7.50-7.62 (m, 2H), 4.29 (s, 3H), 4.25 (q, J=7.1 Hz, 2H), 1.14 (t, J=7.1 Hz, 3H).

Step 4: Preparation of 5-(4-bromo-2-fluoro-phenyl)-3-methyl-3H-[1,2,3]triazole-4-carboxylic acid In a 250 mL round-bottomed flask, 5-(4-bromo-2-fluorophenyl)-3-methyl-3H-[1,2,3]triazole-4-carboxylic acid ethyl ester (291 mg, 887 μmol) was combined with tetrahydrofuran (18 mL) to give a colorless solution. 1M LiOH (9 mL, 9.00 mmol, Eq: 10.1) was added and the reaction was stirred at 25° C. for 15 h. The crude reaction mixture was concentrated in vacuo and acidified with 10 mL of 1M HCl. The reaction was diluted with EtOAc and the organic layer was washed with H₂O (1×20 mL) and saturated NaCl (1×20 mL), dried over Na₂SO₄ and concentrated in vacuo. The white powder was dried under vacuum to afford 266 mg (100%) of the desired product. (M–H)⁻=297.8 and 299.9 (m/e).
$^1$H NMR (DMSO-d₆) $^1$H NMR (DMSO-d₆) δ ppm 13.54-14.48 (br s, 1H), 7.64-7.84 (m, 1H), 7.42-7.63 (m, 2H), 4.27 (s, 3H).

Step 5: Preparation of [5-(4-bromo-2-fluoro-phenyl)-3-methyl-3H-[1,2,3]triazole-4-yl]-carbamic acid (R)-1-phenyl ethyl ester In a 20 mL sealed vial, 5-(4-bromo-2-fluoro-phenyl)-3-methyl-3H-[1,2,3]triazole-4-carboxylic acid (102 mg, 340 μmol), (R)-1-phenylethanol (83.0 mg, 82.1 μL, 680 μmol, Eq: 2) and TEA (86.0 mg, 118 μL, 850 μmol, Eq: 2.5) were combined with toluene (4 ml) to give a colorless solution. DPPA (196 mg, 154 μL, 714 μmol, Eq: 2.1) was added and the reaction mixture was heated to 65° C. under argon for 1.5 h. The reaction was cooled and concentrated in vacuo. The oily residue was purified by flash chromatography (silica gel, 40 g, 0% to 50% EtOAc in heptane) to afford, after drying under vacuum, 83 mg (58%) of the desired product as a white powder. (M+H)⁺=419.0 and 420.9 (m/e). $^1$H NMR (DMSO-d₆) δ ppm 9.32-10.12 (m, 1H), 6.60-7.99 (m, 8H), 5.47-5.98 (m, 1H), 3.91 (s, 3H), 1.33-1.65 (m, 3H).

Step 6: Preparation of 1-{3'-fluoro-4'-[1-methyl-5-((R)-1-phenyl-ethoxycarbonylamino)-1H-[1,2,3]triazole-4-yl]-biphenyl-4-yl}-cyclopropanecarboxylic acid methyl ester To a mixture of [5-(4-bromo-2-fluoro-phenyl)-3-methyl-3H-[1,2,3]triazole-4-yl]-carbamic acid (R)-1-phenyl ethyl ester (237 mg, 565 μmol), 4-(1-(methoxycarbonyl)cyclopropyl)phenylboronic acid (124 mg, 565 μmol), S-Phos (69.6 mg, 170 μmol, Eq: 0.30) and K₃PO₄ (360 mg, 1.7 mmol, Eq: 3.00) in a sealed vial was added toluene (6 mL) and water (1 mL). Pd(OAc)₂ (19.0 mg, 84.8 μmol, Eq: 0.15) was added and the yellow suspension was purged with argon and sealed. The reaction mixture was heated to 105° C. for 2 h and then cooled. LC/MS indicated incomplete reaction. 4-(1-(Methoxycarbonyl)cyclopropyl)phenylboronic acid (49.8 mg, 226 μmol, Eq: 0.4) was added, the reaction was purged with argon and heated at 105° C. for 30 min. The reaction was cooled and diluted with EtOAc and 50% brine. The suspension was filtered and the organic phase was washed with 50% brine. The organic layer was dried over Na₂SO₄ and concentrated in vacuo. The crude material was purified by flash chromatography (silica gel, 40 g, 0% to 80% EtOAc in heptane) to afford 107 mg (37%) of the desired product as a white foam. (M+H)⁺=515.2 (m/e); $^1$H NMR (DMSO-d₆) δ ppm 9.92 (br. s., 1H), 7.64-7.87 (m, 3H), 7.60 (d, J=6.6 Hz, 2H), 7.37-7.51 (m, 5H), 7.32 (br. s., 2H), 5.75 (br. s., 1H), 3.79-4.01 (m, 3H), 3.58 (s, 3H), 1.44-1.63 (m, 4H), 1.20-1.33 (m, 3H).

Example 11

1-{3'-Fluoro-4'-[1-methyl-5-((R)-1-phenyl-ethoxycarbonylamino)-1H-[1,2,3]triazole-4-yl]-biphenyl-4-yl}-cyclopropanecarboxylic acid

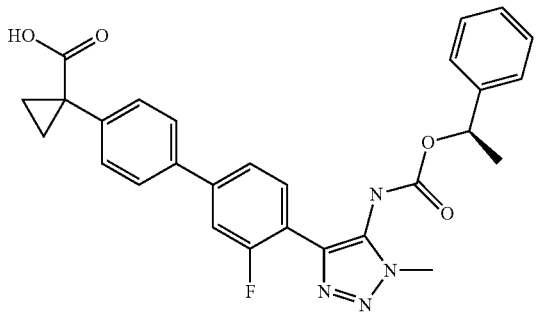 [SMILES: C[C@@H](OC(=O)Nc1c(-c2ccc(-c3ccc(C4(C(=O)O)CC4)cc3)cc2F)nnn1C)c1ccccc1]

In a 250 ml, round-bottomed flask, 1-{3'-fluoro-4'-[1-methyl-5-((R)-1-phenyl-ethoxycarbonylamino)-1H-[1,2,3]triazole-4-yl]-biphenyl-4-yl}-cyclopropanecarboxylic acid methyl ester (95 mg, 185 μmol) was combined with tetrahydrofuran (5 mL) and methanol (1.5 mL) to give a light yellow solution. 1M LiOH (1.85 mL, 1.85 mmol, Eq: 10) was added and the reaction was stirred at 25° C. for 22 h. The crude reaction mixture was concentrated in vacuo, acidified with 1M HCl and extracted with dichloromethane. The aqueous layer was back-extracted with dichloromethane (1×15 mL), dried over $Na_2SO_4$ and concentrated in vacuo. The crude material was purified by flash chromatography (silica gel, 24 g, 0% to 10% methanol in dichloromethane) to afford 85 mg (92%) of the desired product as a white powder. (M+H)'= 501.1 (m/e). $^1$H NMR (DMSO-$d_6$) δ ppm 12.39 (br. s., 1H), 9.92 (br. s., 1H), 7.64-7.78 (m, 3H), 7.59 (d, J=7.8 Hz, 2H), 7.37-7.50 (m, 5H), 7.02-7.37 (m, 2H), 5.74 (br. s., 1H), 3.89 (s, 3H), 1.41-1.60 (m, 4H), 1.09-1.32 (m, 3H).

Example 12

{5-[4'-(1-Methanesulfonylaminocarbonyl-cyclopropyl)-biphenyl-4-yl]-3-methyl-3H-[1,2,3]triazol-4-yl}-carbamic acid (R)-1-phenyl-ethyl ester

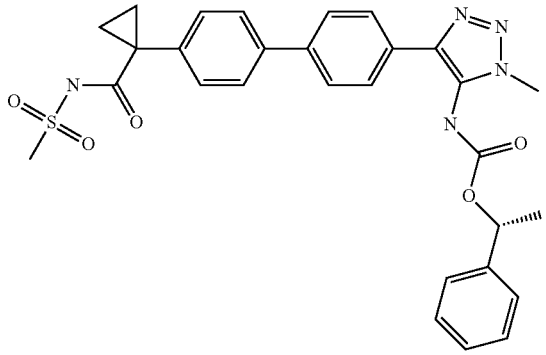 [SMILES: C[C@@H](OC(=O)Nc1c(-c2ccc(-c3ccc(C4(C(=O)NS(C)(=O)=O)CC4)cc3)cc2)nnn1C)c1ccccc1]

Step 1: Preparation of N-[1-(4-bromo-phenyl)-cyclopropanecarbonyl]-methanesulfonamide In a 100 ml, round-bottomed flask, 1-(4-bromo-phenyl)-cyclopropanecarboxylic acid (4 g, 16.6 mmol) was combined with DCM (15 mL) and 3 drops of DMF to give a white suspension. To this was added drop wise a clear solution of oxalyl chloride (6.96 g, 4.8 mL, 54.8 mmol) dissolved in DCM (6 mL). After 10 min, the mixture became clear and the reaction was stirred at room temperature for 2 hr. The reaction was concentrated, dried from toluene and hexanes, and stored in a freezer overnight. In a 200 mL round-bottomed flask, NaH (60% mineral dispersion, 876 mg, 36.5 mmol) was washed with hexanes and the resulting solid was diluted with DMF (6 mL) to give a white suspension. The suspension was cooled in an ice bath and methanesulfonamide (3.16 g, 33.2 mmol) dissolved in DMF (6 mL) was added drop wise under nitrogen. After addition (5 min) the ice bath was removed and the reaction was warmed to room temperature overnight. The reaction was cooled in an ice bath, the acid chloride previously prepared and dissolved in DMF (6 mL) was added drop wise, and the reaction was warmed to room temperature overnight. The reaction was diluted with 0.2 N HCl (200 mL) and extracted with EtOAc (2×100 mL). The organic layers were washed with brine, combined, dried over $MgSO_4$, and concentrated. The crude material was dissolved in minimal DCM and purified by flash chromatography (silica gel, 0% to 60% EtOAc in hexanes, 0.5% AcOH). The appropriate fractions were combined, concentrated, and dried from DCM/hexanes yielding N-[1-(4-bromo-phenyl)-cyclopropanecarbonyl]-methanesulfonamide (2.74 g, 51.9% yield) as a white solid. LC/MS calcd. for $C_{11}H_{12}BrNO_3S$ (m/e) 317/319, obsd. 318/320 (M+H, ES$^+$).

Step 2: Preparation of N-{1-[4-(4,4,5,5-tetramethyl-[1,3,2]dioxaborolan-2-yl)-phenyl]-cyclopropanecarbonyl}-methanesulfonamide In a 350 ml, reaction vial containing N-[1-(4-bromo-phenyl)-cyclopropanecarbonyl]-methanesulfonamide (2.71 g, 8.52 mmol) was added bis-pinacolatodiboron (3.24 g, 12.8 mmol, potassium acetate (2.51 g, 25.6 mmol, Eq: 3) and 1,4 dioxane (63.8 mL) to give a white suspension. The mixture was purged with nitrogen for 20 min and then $PdCl_2$(dppOCH$_2$Cl$_2$ (701 mg, 859 μmol) was added. The vial was sealed and heated in an oil bath at 80° C. for 16 hr. The reaction was diluted with EtOAc (150 mL), filtered, rinsed with 0.2 M HCl (200 mL) and EtOAc (50 mL). The combined filtrate was mixed vigorously, filtered, and separated. The aqueous layer was extracted once with EtOAc (150 mL). The organic layers were washed with brine, combined, dried over $MgSO_4$, filtered, concentrated, and dried from DCM/hexanes to give a brown solid (4 g). The crude material was supported on Celite and purified by flash chromatography (silica gel, 0 to 60% EtOAc in hexanes, 0.5% AcOH). The appropriate fractions were combined, concentrated, and dried from DCM/Hexanes to yield N-{1-[4-(4,4,5,5-tetramethyl-[1,3,2]dioxaborolan-2-yl)-phenyl]-cyclopropanecarbonyl}-methanesulfonamide (2.75 g, 88.4% yield) as a white solid. LC/MS calcd. for $C_{17}H_{24}BNO_5S$ (m/e) 365, obsd. 366 (M+H, ES$^+$).

Step 3: Preparation of {5-[4'-(1-methanesulfonylaminocarbonyl-cyclopropyl)-biphenyl-4-yl]-3-methyl-3H-[1,2,3]triazol-4-yl}-carbamic acid (R)-1-phenyl-ethyl ester In a 20 mL vial, [5-(4-bromo-phenyl)-3-methyl-3H-[1,2,3]triazol-4-yl]-carbamic acid (R)-1-phenyl-ethyl ester (Example 1, 110.3 mg, 275 μmol), N-{1-[4-(4,4,5,5-tetramethyl-[1,3,2]dioxaborolan-2-yl)-phenyl]-cyclopropanecarbonyl}-methanesulfonamide (112 mg, 307 μmol), DPPF (38 mg, 68.5 μmol) and $PdCl_2$(dppf)CH$_2$Cl$_2$ (39 mg, 47.8 μmol) were combined with DMF (5 mL) and the mixture was bubbled with nitrogen for 20 minutes to give a light brown/red solution. To this was added 2N $Na_2CO_3$ (550 μL, 1.1 mmol, degassed with nitrogen bubbled through for 20 min), and the red mixture (looked like salt precipitated) had nitrogen bubbled through for 1 min. The vial was sealed, placed in a dry block, and heated at 80° C. for 4 hr. The reaction was diluted with ethyl acetate (75 mL) and 0.1 M HCl (100 mL), and the layers were separated. The aqueous layer was extracted with ethyl acetate (75 mL). The organic layers were washed with brine, dried over $MgSO_4$, filtered, concentrated, and dried from DCM/hexanes to give a crude material (311 mg). The crude material was dissolved in minimal DCM and purified by flash chromatography (silica gel, 24 g Redisep, 30 mL/min, 0% to 100% EtOAc in hexanes, 0.5% AcOH). Appropriate fractions were combined, concentrated, dried from DCM/hexanes and DCM to yield {5-[4'-(1-methanesulfonylaminocarbonyl-cyclopropyl)-biphenyl-4-yl]-3-methyl-3H-[1,2,3]triazol-4-yl}-carbamic acid (R)-1-phenyl-ethyl ester (98.5 mg, 64% yield). LC/MS calcd. for $C_{29}H_{29}N_5O_5S$ (m/e) 559, obsd. 560 (M+H, ES$^+$). $^1$H NMR (DMSO-d$_6$) δ ppm 11.16 (br. s., 1H), 9.93 (br. s., 1H), 7.80 (d, J=7.8 Hz, 2H), 7.62-7.76 (m, 4H), 7.06-7.57 (m, 7H), 5.65-5.93 (m, 1H), 3.85 (s, 3H), 3.20 (s, 3H), 1.38-1.76 (m, 5H), 1.20 (br. s., 2H).

Example 13

{5-[4'-(1-Methanesulfonylaminocarbonyl-cyclopropyl)-biphenyl-4-yl]-3-methyl-3H-[1,2,3]triazol-4-yl}-carbamic acid (R)-1-(3-trifluoromethyl-phenyl)-ethyl ester

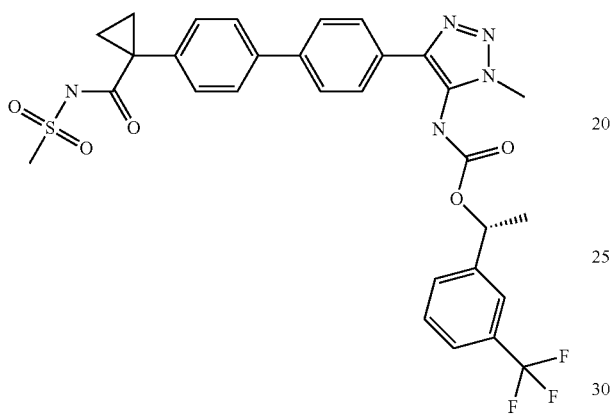

In a 20 ml, vial, 5-(4-bromo-phenyl)-3-methyl-3H-[1,2,3]triazole-4-carboxylic acid (114.3 mg, 405 μmol), (R)-1-(3-(trifluoromethyl)phenyl)ethanol (84.8 mg, 446 μmol) and triethylamine (90.2 mg, 124 μL, 891 μmol) were combined with toluene (5 mL) to give a colorless solution and to this was added DPPA (167 mg, 131 μL, 608 μmol). The reaction vial was sealed, heated in a dry block at 65° C. for 3 hr, and allowed to cool to room temperature overnight. The reaction was concentrated, dried from DCM/hexanes, dissolved in minimal DCM and purified by flash chromatography (silica gel, 0% to 60% EtOAc in hexanes). Appropriate fractions were combined, concentrated, dried from DCM/hexanes to yield [5-(4-bromo-phenyl)-3-methyl-3H-[1,2,3]triazol-4-yl]-carbamic acid (R)-1-(3-trifluoromethyl-phenyl)-ethyl ester (130 mg, 68.4% yield) as a white solid. LC/MS calcd. for $C_{19}H_{16}BrF_3N_4O_2$ (m/e) 468/470, obsd. 469/471 (M+H, ES$^+$).

In a 20 mL vial, [5-(4-bromo-phenyl)-3-methyl-3H-[1,2,3]triazol-4-yl]-carbamic acid (R)-1-(3-trifluoromethyl-phenyl)-ethyl ester (123.7 mg, 264 μmol), N-{1-[4-(4,4,5,5-tetramethyl-[1,3,2]dioxaborolan-2-yl)-phenyl]-cyclopropanecarbonyl}-methanesulfonamide (110 mg, 301 μmol), DPPF (36 mg, 64.9 μmol) and PdCl$_2$(dppOCH$_2$Cl$_2$ (40 mg, 49.0 μmol) were combined with DMF (5 mL, with nitrogen bubbled through for 20 min) to give a light brown/red solution. To this was added 2N Na$_2$CO$_3$ (527 μl, 1.05 mmol, with nitrogen bubbled through for 20 min), the red mixture (looked like salt precipitated) had nitrogen bubbled through for 1 min. The vial was sealed, placed in a dry block, and heated at 80° C. for 4 hr. The reaction was diluted with ethyl acetate (75 mL) and 0.1 M HCl (100 mL). The layers were separated. The aqueous layer was extracted with ethyl acetate (75 mL). The organic layers were washed with brine, dried over MgSO$_4$, filtered, concentrated, and dried from DCM/hexanes to give a crude material (311 mg). The crude material was dissolved in minimal DCM and purified by flash chromatography (silica gel, 24 g Redisep, 30 mL/min, 0% to 100% EtOAc in hexanes, 0.5% AcOH). Appropriate fractions were combined, concentrated, dried from DCM/hexanes to yield {5-[4'-(1-methane-sulfonylamino carbonyl-cyclopropyl)-biphenyl-4-yl]-3-methyl-3H-[1,2,3]triazol-4-yl}-carbamic acid (R)-1-(3-trifluoromethyl-phenyl)-ethyl ester (69.2 mg, 41.8% yield) as a brown solid. $C_{30}H_{28}F_3N_5O_5S$ (m/e) 627, obsd. 628 (M+H, ES$^+$). $^1$H NMR (DMSO-d$_6$) δ ppm 11.16 (br. s., 1H), 9.47-10.15 (m, 1H), 7.53-7.94 (m, 10H), 7.41 (d, J=8.3 Hz, 2H), 5.89 (br. s., 1H), 3.86 (br. s., 3H), 3.20 (s, 3H), 1.60 (br. s., 3H), 1.47-1.53 (m, 2H), 1.20 (d, J=1.8 Hz, 2H).

Example 14

(4-{4-[1-Methyl-5-((R)-1-phenyl-ethoxycarbonylamino)-1H-[1,2,3]triazol-4-yl]-phenyl}-cyclohexyl)-acetic acid

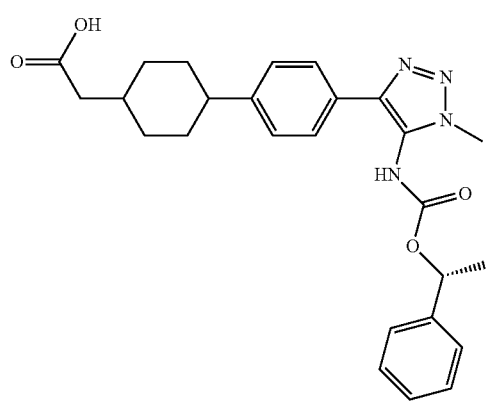 [SMILES: C[C@@H](OC(=O)Nc1c(-c2ccc(C3CCC(CC(=O)O)CC3)cc2)nnn1C)c1ccccc1]

Step 1: Preparation of 5-(4-bromophenyl)-3-methyl-3H-[1,2,3]triazole-4-carboxylic acid benzyl ester To a suspension of 5-(4-bromophenyl)-3-methyl-3H-[1,2,3]triazole-4-carboxylic acid (209 mg, 0.74 mmol) and sodium bicarbonate (187 mg, 2.22 mmol) in DMF (10 mL) was added an excess of benzyl bromide (380 mg, 264 μL, 2.22 mmol) at room temperature under nitrogen atmosphere. The resulting colorless reaction mixture was stirred for 15 h at which time LC/MS and TLC analysis indicated the absence of starting material. The mixture was diluted with water and extracted with ethyl acetate (2×70 mL). The combined extracts were washed with brine solution and dried over anhydrous MgSO$_4$. Filtration and concentration gave the crude colorless oil which was purified using an ISCO (40 g) column chromatography eluting with ethyl acetate in hexanes (0-60%). The desired fractions were collected and the solvent was removed under vacuum to isolate the 5-(4-bromophenyl)-3-methyl-3H-[1,2,3]triazole-4-carboxylic acid benzyl ester as a viscous oil (275 mg, 99% yield). LC/MS calcd. for $C_{17}H_{14}BrN_3O_2$ (m/e) 373, obsd. 373.8 [M+H, ES$^+$].

Step 2: Preparation of 2-(4-idocyclohexyl)acetic acid ethyl ester

To a mixture of 2-(4-hydroxycyclohexyl)acetic acid ethyl ester (3 g, 16.1 mmol), iodine (6.13 g, 24.2 mmol), imidazole (1.64 g, 24.2 mmol), and triphenylphosphine (6.34 g, 24.2 mmol) was added dichloromethane (100 mL) at room temperature under nitrogen atmosphere. The resulting brown suspension was stirred for 15 h at which time TLC analysis indicated the absence of starting material. Then, the solvent was removed under vacuum and most of the residue was dissolved in ethyl acetate (~500 mL) and some of the residue was not dissolved which was found to be Ph$_3$PO by $^1$H NMR. The ethyl acetate solution was washed two times with a solution of water and methanol (3:1) to remove the remaining triphenylphosphineoxide and then washed with brine solution. The organic layer was dried over anhydrous MgSO$_4$, filtered, and concentrated to give the crude residue which was purified using an ISCO (120 g) column chromatography eluting with ethyl acetate in hexanes (0-50%). The desired fractions were combined and the solvent was removed under vacuum to obtain 2-(4-iodocyclohexyl)acetic acid ethyl ester (3.39 g, 71.1% yield) as a viscous light yellow oil. $^1$H NMR of this product indicated that it contained 30-40% of elimination product (olefin) which was not separable on TLC.

Step 3: Preparation of 5-[4-(4-ethoxycarbonylmethyl-cyclohexyl)-phenyl]-3-methyl-3H-[1,2,3]triazole-4-carboxylic acid benzyl ester In a 3-neck 50 mL RB flask, equipped with an additional funnel and thermometer, was charged with zinc dust, 99.9% (490 mg, 7.5 mmol) at room temperature under nitrogen atmosphere. Then, the funnel was purged with nitrogen under vacuum and THF (2 mL) was added to cover the zinc dust. 1,2-Dibromoethane (60.6 mg, 27.8 µL, 0.322 mmol) was added and the mixture was heated with heat gun until evolution of ethylene gas ceased. Then, the suspension was cooled to room temperature and chlorotrimethylsilane (35.0 mg, 40.8 µL, 0.322 mmol) was added and the mixture was stirred for 15 min at room temperature. Then, a solution of 2-(4-iodocyclohexyl)acetic acid ethyl ester (740 mg, 2.5 mmol) in THF (2 mL and 1 mL for washing) was added drop-wise for 5 minutes. After addition, the reaction mixture was heated to ~60° C. with oil bath and stirred for 3 h by which time TLC analysis of the hydrolyzed reaction mixture indicated the absence of the starting material. Then, the heating was stopped and the excess zinc dust was allowed to settle (15 h) to give a colorless solution.

In another 2-neck 25 mL RB flask, palladium(II) acetate (18.1 mg, 0.081 mmol) and 2-dicyclohexylphosphino-2',6'-dimethoxybiphenyl (66.2 mg, 0.162 mmol) were charged and the flask was purged with nitrogen gas. Then, THF (1 mL) was added and the resulting light brown suspension was stirred for 5 min before the addition of a solution of 5-(4-bromophenyl)-3-methyl-3H-[1,2,3]triazole-4-carboxylic acid benzyl ester (120 mg, 0.322 mmol) in THF (3 mL) at room temperature under nitrogen atmosphere. Then, the above prepared colorless zinc solution was added to this mixture. During the addition, it turned to a brown solution which was then heated to 60° C. and stirred for 5 h at which time TLC analysis of the hydrolyzed reaction mixture indicated the absence of starting material. Then, it was cooled to room temperature and diluted with saturated ammonium chloride solution and ethyl acetate. The two layers were separated and the aqueous layer was extracted with ethyl acetate. The combined organic extracts were washed with brine solution and dried over anhydrous MgSO$_4$. Filtration of the drying agent and concentration of the filtrate gave the crude light yellow residue which was purified using an ISCO (80 g) column eluting with ethyl acetate in hexanes (0-100%). The desired fractions were combined and the solvent was removed under vacuum to obtain 5-[4-(4-ethoxycarbonylmethyl-cyclohexyl)-phenyl]-3-methyl-3H-[1,2,3]triazole-4-carboxylic acid benzyl ester (55 mg, 37.0% yield) as a light brown oil. LC/MS calcd. for $C_{27}H_{31}N_3O_4$ (m/e) 461, obsd. 462.1 [M+H, ES$^+$].

Step 4: Preparation of 5-[4-(4-ethoxycarbonylmethyl-cyclohexyl)-phenyl]-3-methyl-3H-[1,2,3]triazole-4-carboxylic acid To a mixture of 5-[4-(4-ethoxycarbonylmethyl-cyclohexyl)-phenyl]-3-methyl-3H-[1,2,3]triazole-4-carboxylic acid benzyl ester (51 mg, 0.11 mmol) and 10% Pd/C (58.8 mg, 0.552 mmol) was added ethyl acetate (5 mL) at room temperature under nitrogen atmosphere. Then, the nitrogen was replaced with a hydrogen gas balloon and the black reaction mixture was stirred for 15 h under hydrogen atmosphere at which time TLC analysis indicated the absence of the starting material. Then, the reaction mixture was filtered and the charcoal was washed with a hot ethyl acetate (50 mL), THF (25 mL), CH$_3$CN (75 mL), and ethanol (25 mL). The filtrate was concentrated under vacuum and the residue was dried under high vacuum to obtain 5-[4-(4-ethoxycarbonylmethyl-cyclohexyl)-phenyl]-3-methyl-3H-[1,2,3]triazole-4-carboxylic acid (40 mg, 97.5% yield) as a white solid. LC/MS calcd. for $C_{20}H_{25}N_3O_4$ (m/e) 371, obsd. 372.3 [M+H, ES$^+$].

Step 5: Preparation of (4-{4-[1-methyl-5-((R)-1-phenyl-ethoxycarbonylamino)-1H-[1,2,3]triazol-4-yl]-phenyl}-cyclohexyl)-acetic acid ethyl ester To a light brown solution of 5-[4-(4-ethoxycarbonylmethyl-cyclohexyl)-phenyl]-3-methyl-3H-[1,2,3]triazole-4-carboxylic acid (37 mg, 0.099 mmol) in toluene (5 mL) was added triethylamine (20.2 mg, 27.8 µL, 0.199 mmol) at room temperature. To the resulting solution was added diphenylphosphoryl azide (30.2 mg, 23.6 µL, 0.11 mmol) followed by (R)-1-phenylethanol (13.4 mg, 13.2 µL, 0.11 mmol) at room temperature. The resulting solution was heated with oil bath to 81° C. and stirred for 1 h at which time TLC analysis indicated the absence of the starting material. Then, the reaction mixture was cooled to room temperature and the solvent was removed under vacuum. The crude residue was treated with dichloromethane (10 mL) and filtered. The filtrate was loaded onto an ISCO (40 g) column chromatography eluting with ethyl acetate in hexanes (0-100%). The desired fractions were combined and the solvent was removed under vacuum to obtain (4-{4-[1-methyl-5-((R)-1-phenyl-ethoxycarbonylamino)-1H-[1,2,3]triazol-4-yl]-phenyl}-cyclohexyl)-acetic acid ethyl ester (17 mg, 35% yield) as a white solid. LC/MS calcd for $C_{28}H_{34}N_4O_4$ (m/e) 490, obsd. 491.3 [M+H, ES$^+$].

Step 6: Preparation of (4-{4-[1-methyl-5-((R)-1-phenyl-ethoxycarbonylamino)-1H-[1,2,3]triazol-4-yl]-phenyl}-cyclohexyl)-acetic acid To a solution of (4-{4-[1-methyl-5-((R)-1-phenyl-ethoxycarbonylamino)-1H-[1,2,3]triazol-4-yl]-phenyl}-cyclohexyl)-acetic acid ethyl ester (15 mg, 0.031 mmol) in THF (2 mL) and ethanol (2 mL) was added a 1.0 M solution of sodium hydroxide (310 µL, 0.31 mmol) at room temperature. The resulting colorless solution was stirred for 15 h at which time TLC analysis indicated the absence of the starting material. Then, the solvent was removed under vacuum and the basic aqueous layer was neutralized with 1 N HCl. The resulting solids were collected by filtration and washed with water and hexanes. After air drying, (4-{4-[1-methyl-5-((R)-1-phenyl-ethoxycarbonylamino)-1H-[1,2,3]triazol-4-yl]-phenyl}-cyclohexyl)-acetic acid (10 mg, 71% yield) was isolated as a white solid. $^1$H NMR (DMSO-$d_6$) δ ppm 12.04 (br. s., 1H), 9.85 (br. s., 1H), 7.62 (d, J=7.3 Hz, 2H), 6.84-7.54 (m, 7H), 5.78 (br. s., 1H), 3.83 (s, 3H), 2.16 (d, J=6.8 Hz, 2H), 1.65-1.93 (m, 5H), 1.39-1.64 (m, 5H), 1.01-1.35 (m, 3H). LC/MS calcd. for $C_{26}H_{30}N_4O_4$ (m/e) 462, obsd. 463.3 [M+H, ES$^+$].

Example 15

Calcium Flux Assay Using Fluorometric Imaging Plate Reader (FLIPR)

Cell Culture Conditions: The ChemiScreen Calcium-optimized stable cell line containing the human recombinant LPA1 Lysophospholipid receptor was purchased from Chemicon International, Inc./Millipore. The cells were cultured in DMEM-high glucose supplemented with 10% fetal bovine serum, 2 mM glutamine, 100 U/mL penicillin/100 µg/mL streptomycin, 1× non-essential amino acids, 10 mM HEPES and 0.25 mg/mL Geneticin. Cells were harvested with trypsin-EDTA and counted using ViaCount reagent. The cell suspension volume was adjusted to 2.0×10$^5$ cells/mL with complete growth media. Aliquots of 50 µL were dispensed into 384 well black/clear tissue culture treated plates (BD) and the microplates were placed in a 37° C. incubator overnight. The following day plates were used in the assay.

Dye Loading and Assay: Loading Buffer (FLIPR Calcium-4, Molecular Devices) was prepared by dissolving the contents of one bottle into 100 mL Hank's Balanced Salt Solution containing 20 mM HEPES and 2.5 mM probenecid. Plates were loaded onto Biotek plate washer and growth media was removed and replaced with 20 µL of Hank's Balanced Salt Solution containing 20 mM HEPES and 2.5 mM probenecid, followed by 25 µL of Loading Buffer. The plates were then incubated for 30 minutes at 37° C.

During the incubation, test compounds were prepared by adding 90 µL of HBSS/20 mM HEPES/0.1% BSA buffer to 2 µL of serially diluted compounds. To prepare serial dilutions, 10 mM stocks of compounds were prepared in 100% DMSO. The compound dilution plate was set up as follows: well #1 received 29 µL of stock compound and 31 µL DMSO. Wells 2-10 received 40 µL of DMSO. After mixing, 20 µL of solution from well #1 was transferred into well #2, followed by 1:3 serial dilutions out 10 steps. 2 µL of diluted compound was transferred into duplicate wells of 384 well "assay plate" and then 90 µL of buffer was added.

After incubation, both the cell and "assay" plates were brought to the FLIPR and 20 µL of the diluted compounds were transferred to the cell plates by the FLIPR. Compound addition was monitored by the FLIPR to detect any agonist activity of the compounds. Plates were then incubated for 30 minutes at room temperature protected from light. After the incubation, plates were returned to the FLIPR and 20 µL of 4.5× concentrated agonist was added to the cell plates. During the assay, fluorescence readings were taken simultaneously from all 384 wells of the cell plate every 1.5 seconds. Five readings were taken to establish a stable baseline, then 20 µL of sample was rapidly (30 µL/sec) and simultaneously added to each well of the cell plate. The fluorescence was continuously monitored before, during and after sample addition for a total elapsed time of 100 seconds. Responses (increase in peak fluorescence) in each well following agonist addition was determined. The initial fluorescence reading from each well, prior to ligand stimulation, was used as zero baseline value for the data from that well. The responses were expressed as % inhibition of the buffer control. The IC$_{50}$ value, defined as the concentration of a compound that is required for 50% inhibition of the buffer control, was calculated by fitting the percent inhibition data for 10 concentrations to a sigmoidal dose-response (4 parameter logistic) model using Genedata Condoseo program [model 205, F(x)= (A+(B−A)/(1+((C/x)^D)))]. The antagonist activities of representative compounds of the invention are provided in Table 1 below:

TABLE 1

| | LPAR1 and LPAR3 antagonist activities | |
|---|---|---|
| Example # | LPAR1 IC$_{50}$ (µM) or (inhibition % @µM) | LPAR3 IC$_{50}$ (µM) or (inhibition % @µM) |
| 1 | 21.91 (52.3%% @ 30) | >30 |
| 2 | 0.018 | 2.29 |
| 3 | 0.048 | 21.94 (58.2% @ 30) |
| 4 | 0.046 | 0.279 |
| 5 | 2.66 | 6.31 |
| 6 | 0.018 | 0.132 |
| 7 | 0.07 | >30 |
| 8 | >30 | >30 |
| 9 | 4.45 | 18.43 (62.0% @ 30) |
| 10 | >30 | >30 |
| 11 | 0.018 | 27.35 (62% @ 30) |
| 12 | 0.0188 | 2.31 |
| 13 | 0.0245 | 0.0657 |
| 14 | 0.058 | 18.64 (68% @ 30) |

It is to be understood that the invention is not limited to the particular embodiments of the invention described above, as variations of the particular embodiments may be made and still fall within the scope of the appended claims.

The invention claimed is:
1. A compound of formula (I):

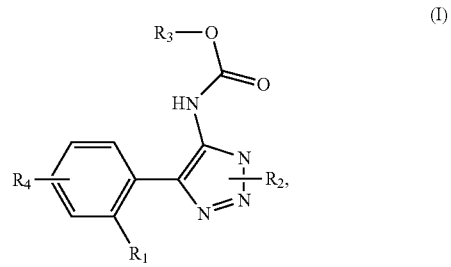

wherein:
R$_1$ is hydrogen or halogen;
R$_2$ is unsubstituted lower alkyl;
R$_3$ is unsubstituted lower alkyl, lower alkyl substituted with unsubstituted phenyl or lower alkyl substituted with phenyl substituted with trifluoromethyl; and
R$_4$ is hydrogen, halogen, cycloalkyl acetic acid, unsubstituted phenyl or phenyl substituted with a moiety selected from acetic acid, cyclopropanecarboxylic acid, cyclopropanecarboxylic acid methyl ester, methanesulfonylaminocarbonyl-cyclopropane or cyclopropyltetrazole, or a pharmaceutically acceptable salt thereof.

2. The compound according to claim 1, wherein R$_1$ is hydrogen or halogen; R$_2$ is unsubstituted lower alkyl; R$_3$ is unsubstituted lower alkyl, lower alkyl substituted with unsubstituted phenyl or lower alkyl substituted with phenyl substituted with trifluoromethyl; and R$_4$ is phenyl substituted with methanesulfonylaminocarbonyl-cyclopropane, or a pharmaceutically acceptable salt thereof.

3. The compound according to claim 1, wherein $R_1$ is hydrogen.

4. The compound according to claim 1, wherein $R_1$ is bromine or fluorine.

5. The compound according to claim 1, wherein $R_2$ is methyl.

6. The compound according to claim 1, wherein $R_3$ is ethyl or dimethylpropyl.

7. The compound according to claim 1, wherein $R_3$ is ethyl substituted with unsubstituted phenyl.

8. The compound according to claim 1, wherein $R_3$ is ethyl substituted with phenyl substituted with trifluoromethyl.

9. The compound according to claim 1, wherein $R_4$ is hydrogen, bromine or unsubstituted phenyl.

10. The compound according to claim 1, wherein $R_4$ is phenyl substituted with a moiety selected from acetic acid, cyclopropanecarboxylic acid or cyclopropanecarboxylic acid methyl.

11. The compound according to claim 1, wherein said compound is:

[5-(4-Bromo-phenyl)-3-methyl-3H-[1,2,3]triazol-4-yl]-carbamic acid (R)-1-phenyl-ethyl ester;

1-{4'-[1-Methyl-5-((R)-1-phenyl-ethoxycarbonylamino)-1H- [1,2,3]triazol-4-yl]-biphenyl-4-yl}-cyclopropanecarboxylic acid;

{4'-[1-Methyl-5-((R)-1-phenyl-ethoxycarbonylamino)-1H-[1,2,3]triazol-4-yl]-biphenyl-4-yl}-acetic acid;

1-(4'-{1-Methyl-5-[1-(3-trifluoromethyl-phenyl)-ethoxycarbonylamino]-1H-[1,2,3]triazol-4-yl}-biphenyl-4-yl)-cyclopropanecarboxylic acid;

1-(4'-{1-Methyl-5-[(S)-1-(3-trifluoromethyl-phenyl)-ethoxycarbonylamino]-1H- [1,2,3]triazol-4-yl}-biphenyl-4-yl)-cyclopropanecarboxylic acid;

1-(4'-{1-Methyl-5-[(R)-1-(3-trifluoromethyl-phenyl)-ethoxycarbonylamino]-1H-[1,2,3]triazol-4-yl}-biphenyl-4-yl)-cyclopropanecarboxylic acid;

1-{4'-[5-((R)-1,2-Dimethyl-propoxycarbonylamino)-1-methyl-1H-[1,2,3]triazol-4-yl]-biphenyl-4-yl}-cyclopropanecarboxylic acid;

1-{4'-[3-Methyl-5-((R)-1-phenyl-ethoxycarbonylamino)-3H-[1,2,3]triazol-4-yl]-biphenyl-4-yl}-cyclopropanecarboxylic acid;

(R)-1-(4'-(1-Methyl-5-((1-phenylethoxy)carbonylamino)-1H-1,2,3-triazol-4-yl)biphenyl-3-yl)cyclopropanecarboxylic acid;

1-{3'-Fluoro-4'-[1-methyl-5-((R)-1-phenyl-ethoxycarbonylamino)-1H-[1,2,3]triazole-4-yl]-biphenyl-4-yl}-cyclopropanecarboxylic acid methyl ester;

1-{3'-Fluoro-4'-[1-methyl-5-((R)-1-phenyl-ethoxycarbonylamino)-1H-[1,2,3]triazole-4-yl]-biphenyl-4-yl}-cyclopropanecarboxylic acid;

{5-[4'-(1-Methanesulfonylaminocarbonyl-cyclopropyl)-biphenyl-4-yl]-3-methyl-3H-[1,2,3]triazol-4-yl}-carbamic acid (R)-1-phenyl-ethyl ester;

{5-[4'-(1 -Methanesulfonylaminocarbonyl-cyclopropyl)-biphenyl-4-yl]-3 -methyl-3H-[1,2,3]triazol-4-yl}-carbamic acid (R)-1-(3-trifluoromethyl-phenyl)-ethyl ester; or (4-{4-[1-Methyl-5-((R)-1-phenyl-ethoxycarbonylamino)-1H-[1,2,3]triazol-4-yl]-phenyl}-cyclohexyl)-acetic acid.

12. A pharmaceutical composition, comprising a therapeutically effective amount of a compound according to claim 1 and a therapeutically inert carrier.

13. A method for the treatment of pulmonary fibrosis, comprising the step of administering an effective amount of a compound according to claim 1 to a patient in need thereof.

\* \* \* \* \*

UNITED STATES PATENT AND TRADEMARK OFFICE
CERTIFICATE OF CORRECTION

PATENT NO. : 9,321,738 B2  
APPLICATION NO. : 14/401009  
DATED : April 26, 2016  
INVENTOR(S) : Stephen Deems Gabriel et al.

It is certified that error appears in the above-identified patent and that said Letters Patent is hereby corrected as shown below:

On the title page

Item 73, "Hoffman-La Roche Inc." should be replaced with "Hoffmann-La Roche Inc."

Signed and Sealed this
Twenty-first Day of June, 2016

Michelle K. Lee
*Director of the United States Patent and Trademark Office*